(12) United States Patent
Donders et al.

(10) Patent No.: US 8,103,349 B2
(45) Date of Patent: *Jan. 24, 2012

(54) NEURAL ELECTRODE TREATMENT

(75) Inventors: Adrianus P. Donders, Andover, MN (US); Koen J. Weijand, Alfaz Del Pi (ES); Mark B. Knudson, Shoreview, MN (US)

(73) Assignee: EnteroMedics Inc., St. Paul, MN (US)

( * ) Notice: Subject to any disclaimer, the term of this patent is extended or adjusted under 35 U.S.C. 154(b) by 120 days.

This patent is subject to a terminal disclaimer.

(21) Appl. No.: 12/638,266

(22) Filed: Dec. 15, 2009

(65) Prior Publication Data

US 2010/0094375 A1    Apr. 15, 2010

Related U.S. Application Data

(63) Continuation of application No. 11/205,415, filed on Aug. 17, 2005, now Pat. No. 7,672,727.

(51) Int. Cl.
*A61N 1/06* (2006.01)
*A61N 1/36* (2006.01)

(52) U.S. Cl. .......................... 607/40; 607/66

(58) Field of Classification Search ............. 607/40, 607/66
See application file for complete search history.

(56) References Cited

U.S. PATENT DOCUMENTS

| | | | |
|---|---|---|---|
| 3,128,760 A | 4/1964 | Baker | |
| 3,411,507 A | 11/1968 | Wingrove | |
| 4,114,625 A | 9/1978 | Onat | |
| 4,198,963 A | 4/1980 | Barkalow et al. | |
| 4,541,432 A | 9/1985 | Molina-Negro et al. | |
| 4,702,254 A | 10/1987 | Zabara | |
| 4,776,349 A | 10/1988 | Nashef et al. | |
| 4,867,164 A | 9/1989 | Zabara | |
| 4,979,511 A | 12/1990 | Terry et al. | |
| 5,025,807 A | 6/1991 | Zabara | |

(Continued)

FOREIGN PATENT DOCUMENTS

EP    1 666 087 A1    2/1998

(Continued)

OTHER PUBLICATIONS

"Bravo™ pH Monitoring System Catheter-Free pH Testing", document No. UC 200300235 EN N15344, Medtronic, Inc., Minneapolis, Minnesota, USA (2002).

(Continued)

*Primary Examiner* — Carl H Layno
*Assistant Examiner* — Jessica Sarcione
(74) *Attorney, Agent, or Firm* — Merchant & Gould P.C.

(57) ABSTRACT

An apparatus for applying a signal to a nerve for the treatment of a disorder includes a first electrode and a second electrode. Each of the electrodes is adapted to be secured to a nerve of a patient. A signal generator is electrically connected to each of the first and second electrodes. The signal generator is adapted to create a signal having a first waveform at the first electrode and a second waveform at the second electrode. The waveforms have parameters selected to block propagation of neural action potentials. The waveforms have a repeating pattern of cycles of pulses with a delay period between at least selected ones of said pulses. In one embodiment, the first and second waveforms are out of phase for a cycle of one of the waveforms to occur during a delay period of the other of the waveforms.

27 Claims, 8 Drawing Sheets

U.S. PATENT DOCUMENTS

| | | |
|---|---|---|
| 5,188,104 A | 2/1993 | Wernicke et al. |
| 5,199,430 A | 4/1993 | Fang et al. |
| 5,215,086 A | 6/1993 | Terry, Jr. et al. |
| 5,215,089 A | 6/1993 | Baker, Jr. et al. |
| 5,226,429 A | 7/1993 | Kuzmak |
| 5,231,988 A | 8/1993 | Wernicke et al. |
| 5,251,634 A | 10/1993 | Weinberg |
| 5,263,480 A | 11/1993 | Wernicke et al. |
| 5,269,303 A | 12/1993 | Wernicke et al. |
| 5,292,344 A | 3/1994 | Douglas |
| 5,299,569 A | 4/1994 | Wernicke et al. |
| 5,330,515 A | 7/1994 | Rutecki et al. |
| 5,335,657 A | 8/1994 | Terry et al. |
| 5,344,438 A | 9/1994 | Testerman |
| 5,370,675 A | 12/1994 | Edwards et al. |
| 5,423,872 A | 6/1995 | Cigaina |
| 5,437,291 A | 8/1995 | Pasricha et al. |
| 5,514,175 A | 5/1996 | Kim et al. |
| 5,531,778 A | 7/1996 | Maschino et al. |
| 5,540,730 A | 7/1996 | Terry, Jr. et al. |
| 5,571,150 A | 11/1996 | Wernicke et al. |
| 5,601,604 A | 2/1997 | Vincent |
| 5,620,955 A | 4/1997 | Knight et al. |
| 5,690,691 A | 11/1997 | Chen et al. |
| 5,707,400 A | 1/1998 | Terry, Jr. et al. |
| 5,716,385 A | 2/1998 | Mittal et al. |
| 5,747,060 A | 5/1998 | Sackler et al. |
| 5,749,907 A | 5/1998 | Mann |
| 5,830,434 A | 11/1998 | Taylor et al. |
| 5,836,994 A | 11/1998 | Bourgeois |
| 5,861,014 A | 1/1999 | Familoni |
| 5,919,216 A | 7/1999 | Houben et al. |
| 5,967,977 A | 10/1999 | Mullis et al. |
| 5,995,872 A | 11/1999 | Bourgeois |
| 6,002,964 A | 12/1999 | Feler et al. |
| 6,083,249 A | 7/2000 | Familoni |
| 6,091,992 A | 7/2000 | Bourgeois et al. |
| 6,093,167 A | 7/2000 | Houben et al. |
| 6,097,984 A | 8/2000 | Douglas |
| 6,098,629 A | 8/2000 | Johnson et al. |
| 6,104,955 A | 8/2000 | Bourgeois |
| 6,111,715 A | 8/2000 | Tsuchiya et al. |
| 6,129,726 A | 10/2000 | Edwards |
| 6,135,978 A | 10/2000 | Houben et al. |
| 6,148,222 A | 11/2000 | Ramsey, III |
| 6,216,039 B1 | 4/2001 | Bourgeois |
| 6,238,423 B1 | 5/2001 | Bardy |
| 6,243,607 B1 | 6/2001 | Mintchev et al. |
| 6,261,280 B1 | 7/2001 | Houben et al. |
| 6,261,572 B1 | 7/2001 | Donovan |
| 6,290,961 B1 | 9/2001 | Aoki et al. |
| 6,292,703 B1 | 9/2001 | Meier et al. |
| 6,308,105 B1 | 10/2001 | Duysens et al. |
| 6,312,708 B1 | 11/2001 | Donovan |
| 6,341,236 B1 | 1/2002 | Osorio et al. |
| 6,364,899 B1 | 4/2002 | Dobak, III |
| 6,369,079 B1 | 4/2002 | Rubin et al. |
| 6,405,732 B1 | 6/2002 | Edwards et al. |
| 6,418,346 B1 | 7/2002 | Nelson et al. |
| 6,449,511 B1 | 9/2002 | Mintchev et al. |
| 6,473,644 B1 | 10/2002 | Terry, Jr. et al. |
| 6,532,388 B1 | 3/2003 | Hill et al. |
| 6,558,708 B1 | 5/2003 | Lin |
| 6,571,127 B1 | 5/2003 | Ben-Haim et al. |
| 6,587,719 B1 | 7/2003 | Barrett et al. |
| 6,587,725 B1 | 7/2003 | Durand et al. |
| 6,591,137 B1 | 7/2003 | Fischell |
| 6,600,956 B2 | 7/2003 | Maschino et al. |
| 6,609,025 B2 | 8/2003 | Barrett et al. |
| 6,610,713 B2 | 8/2003 | Tracey |
| 6,611,715 B1 | 8/2003 | Boveja |
| 6,612,983 B1 | 9/2003 | Marchal |
| 6,622,038 B2 | 9/2003 | Barrett et al. |
| 6,684,105 B2 | 1/2004 | Cohen et al. |
| 6,746,474 B2 | 6/2004 | Saadat |
| 6,760,626 B1 | 7/2004 | Boveja |
| 6,826,428 B1 | 11/2004 | Chen et al. |
| 6,832,114 B1 | 12/2004 | Whitehurst et al. |
| 6,853,862 B1 | 2/2005 | Marchal et al. |
| 6,879,859 B1 | 4/2005 | Boveja |
| 6,895,278 B1 | 5/2005 | Gordon |
| 6,928,320 B2 | 8/2005 | King |
| 6,993,391 B2 | 1/2006 | Flesler et al. |
| 7,054,690 B2 | 5/2006 | Imran |
| 7,072,720 B2 | 7/2006 | Puskas |
| 7,076,307 B2 | 7/2006 | Boveja et al. |
| 7,142,910 B2 | 11/2006 | Puskas |
| 7,167,750 B2 | 1/2007 | Knudson et al. |
| 7,292,890 B2 | 11/2007 | Whitehurst et al. |
| 7,299,091 B2 | 11/2007 | Barrett et al. |
| 7,340,306 B2 | 3/2008 | Barrett |
| 7,346,398 B2 | 3/2008 | Gross et al. |
| 7,389,145 B2 | 6/2008 | Kilgore et al. |
| 7,444,183 B2 | 10/2008 | Knudson et al. |
| 7,444,184 B2 | 10/2008 | Boveja |
| 7,489,969 B2 | 2/2009 | Knudson et al. |
| 7,613,515 B2 | 11/2009 | Knudson et al. |
| 7,620,454 B2 | 11/2009 | Dinsmoor et al. |
| 7,620,455 B2 | 11/2009 | Maschino |
| 7,630,769 B2 | 12/2009 | Knudson |
| 7,672,727 B2 * | 3/2010 | Donders et al. ................. 607/40 |
| 7,693,577 B2 | 4/2010 | Knudson |
| 7,720,540 B2 | 5/2010 | Knudson et al. |
| 7,729,771 B2 | 6/2010 | Knudson |
| 7,822,486 B2 | 10/2010 | Foster et al. |
| 7,844,338 B2 | 11/2010 | Knudson et al. |
| 7,917,226 B2 | 3/2011 | Nghiem et al. |
| 7,986,995 B2 | 7/2011 | Knudson et al. |
| 2001/0012828 A1 | 8/2001 | Aoki et al. |
| 2001/0051787 A1 | 12/2001 | Haller et al. |
| 2002/0016617 A1 | 2/2002 | Oldham |
| 2002/0032468 A1 | 3/2002 | Hill et al. |
| 2002/0052336 A1 | 5/2002 | Yerxa et al. |
| 2002/0055779 A1 | 5/2002 | Andrews |
| 2002/0072780 A1 | 6/2002 | Foley |
| 2002/0087192 A1 | 7/2002 | Barrett et al. |
| 2002/0094962 A1 | 7/2002 | Ashley et al. |
| 2002/0103424 A1 | 8/2002 | Swoyer et al. |
| 2002/0161360 A1 | 10/2002 | Carroll |
| 2002/0198570 A1 | 12/2002 | Puskas |
| 2002/0198571 A1 | 12/2002 | Puskas |
| 2003/0014086 A1 | 1/2003 | Sharma |
| 2003/0018367 A1 | 1/2003 | DiLorenzo |
| 2003/0040785 A1 | 2/2003 | Maschino et al. |
| 2003/0045909 A1 | 3/2003 | Gross et al. |
| 2003/0045914 A1 | 3/2003 | Cohen et al. |
| 2003/0074039 A1 | 4/2003 | Puskas |
| 2003/0135245 A1 | 7/2003 | Campos |
| 2003/0135248 A1 | 7/2003 | Stypulkowski |
| 2003/0144709 A1 | 7/2003 | Zabara et al. |
| 2003/0171789 A1 | 9/2003 | Malek et al. |
| 2003/0181958 A1 | 9/2003 | Dobak, III |
| 2003/0181959 A1 | 9/2003 | Dobak, III |
| 2003/0195601 A1 | 10/2003 | Hung et al. |
| 2003/0212440 A1 | 11/2003 | Boveja |
| 2004/0039425 A1 | 2/2004 | Greenwood-Van Meerveld |
| 2004/0039427 A1 | 2/2004 | Barrett et al. |
| 2004/0059383 A1 | 3/2004 | Puskas |
| 2004/0086531 A1 | 5/2004 | Barron |
| 2004/0089313 A1 | 5/2004 | Utley et al. |
| 2004/0111126 A1 | 6/2004 | Tanagho et al. |
| 2004/0127953 A1 | 7/2004 | Kilgore et al. |
| 2004/0167583 A1 | 8/2004 | Knudson et al. |
| 2004/0172084 A1 | 9/2004 | Knudson et al. |
| 2004/0172085 A1 | 9/2004 | Knudson et al. |
| 2004/0172086 A1 | 9/2004 | Knudson et al. |
| 2004/0172088 A1 | 9/2004 | Knudson et al. |
| 2004/0176812 A1 | 9/2004 | Knudson et al. |
| 2004/0181178 A1 | 9/2004 | Aldrich et al. |
| 2004/0193229 A1 | 9/2004 | Starkebaum et al. |
| 2004/0236381 A1 | 11/2004 | Dinsmoor et al. |
| 2004/0236382 A1 | 11/2004 | Dinsmoor et al. |
| 2004/0243182 A1 | 12/2004 | Cohen et al. |
| 2004/0249416 A1 | 12/2004 | Yun et al. |
| 2004/0254616 A1 | 12/2004 | Rossing et al. |
| 2005/0038484 A1 | 2/2005 | Knudson et al. |
| 2005/0049655 A1 | 3/2005 | Boveja et al. |

| | | | |
|---|---|---|---|
| 2005/0070970 A1 | 3/2005 | Knudson et al. |
| 2005/0070974 A1 | 3/2005 | Knudson et al. |
| 2005/0075693 A1 | 4/2005 | Toy et al. |
| 2005/0131485 A1 | 6/2005 | Knudson et al. |
| 2005/0137644 A1 | 6/2005 | Boveja et al. |
| 2005/0143378 A1 | 6/2005 | Yun et al. |
| 2005/0143412 A1 | 6/2005 | Puskas |
| 2005/0143787 A1 | 6/2005 | Boveja et al. |
| 2005/0149141 A1 | 7/2005 | Starkebaum |
| 2005/0149146 A1 | 7/2005 | Boveja et al. |
| 2005/0149148 A1 | 7/2005 | King |
| 2005/0203501 A1 | 9/2005 | Aldrich et al. |
| 2005/0240231 A1 | 10/2005 | Aldrich et al. |
| 2005/0267542 A1 | 12/2005 | David et al. |
| 2006/0015151 A1 | 1/2006 | Aldrich |
| 2006/0030919 A1 | 2/2006 | Mrva et al. |
| 2006/0036293 A1 | 2/2006 | Whitehurst et al. |
| 2006/0041277 A1 | 2/2006 | Deem |
| 2006/0100668 A1 | 5/2006 | Ben-david et al. |
| 2006/0190053 A1 | 8/2006 | Dobak, III |
| 2006/0212089 A1 | 9/2006 | Tass et al. |
| 2006/0229685 A1 | 10/2006 | Knudson et al. |
| 2006/0247737 A1 | 11/2006 | Olson |
| 2007/0027484 A1 | 2/2007 | Guzman et al. |
| 2007/0043400 A1 | 2/2007 | Donders et al. |
| 2007/0100377 A1 | 5/2007 | Armstrong et al. |
| 2007/0135846 A1 | 6/2007 | Knudson et al. |
| 2007/0135856 A1 | 6/2007 | Knudson et al. |
| 2007/0135857 A1 | 6/2007 | Knudson et al. |
| 2007/0135858 A1 | 6/2007 | Knudson et al. |
| 2007/0142870 A1 | 6/2007 | Knudson et al. |
| 2007/0203521 A1 | 8/2007 | Dobak et al. |
| 2008/0021512 A1 | 1/2008 | Knudson et al. |
| 2008/0300654 A1 | 12/2008 | Lambert et al. |
| 2009/0306739 A1 | 12/2009 | Dilorenzo |

FOREIGN PATENT DOCUMENTS

| | | |
|---|---|---|
| EP | 0 865 800 A2 | 9/1998 |
| EP | 0 896 828 A2 | 2/1999 |
| EP | 1 004 330 A1 | 5/2000 |
| WO | WO 01/41671 A2 | 6/2001 |
| WO | WO 01/43821 A1 | 6/2001 |
| WO | WO 02/26320 A1 | 4/2002 |
| WO | WO 02/065896 | 8/2002 |
| WO | WO 2004/036377 A2 | 4/2004 |
| WO | WO 2004/064918 A1 | 8/2004 |
| WO | WO 2004/082763 A1 | 9/2004 |
| WO | WO 2004/093981 A1 | 11/2004 |
| WO | WO 2004/110551 A2 | 12/2004 |
| WO | WO 2006/023498 | 3/2006 |

OTHER PUBLICATIONS

"Medical Care for Obese Patients", U.S. Department of Health and Human Services, National Institute of Diabetes and Digestive and Kidney Diseases, pp. 1-6, NIH Publication No. 03-5335, Feb. 2003.

"Obesity and Technology: Can the stomach be fooled", Reuters (Apr. 26, 2006), 3 pages, http://news.yahoo.com/s/nm/20060426/us_nm/bizfeature_obesitytechnology_de&printer as printed on May 23, 2006.

Accarino, et al, "Attention and Distraction: Effects on Gut Perception", Gastroenterology, vol. 113, pp. 415-422 (1997).

Accarino, et al, "Gut Perception in Humans Is Modulated by Interacting Gut Stimuli", Am. J. Physiol. Gastrointestinal Liver Physiol., vol. 282, pp. G220-G225 (2002).

Accarino, et al "Modification of Small Bowel Mechanosensitivity by Intestinal Fat", GUT, vol. 48, pp. 690-695 (2001).

Accarino, et al, "Selective Dysfunction of Mechanosensitive Intestinal Afferents in Irritable Bowel Syndrome", Gastroenterology, vol. 108, pp. 636-643 (1994).

Accarino, et al, "Symptomatic Responses to Stimulation of Sensory Pathways in the Jejunum", Am. J. Physiol., vol. 263, pp. G673-G677 (1992).

Aggarwal A, et al., "Predominant Symptoms in Irritable Bowel Syndrome Correlate with Specific Autonomic Nervous System Abnormalities", Gastroenterol, (1994);106:945-950.

Amaris et al., "Microprocessor controlled movement of solid colonic content using sequential neural electrical stimulation", Gut, 50: pp. 475-479 (2002).

Balaji et al., "A Safe and Noninvasice Test for Vagal Integrity Revisited", Archive Surgery, 137:954-959 (2002).

Balemba et al., "Innervation of the extrahepatic biliary tract", The Anatomical Record Part A: Discoveries in Molecular, Cellular, and Evolutionary Biology; 2004: vol. 280A, Issue 1, pp. 836-847.

Bard® Minnesota Four Lumen Esophagogastric Tamponade Tube for the Control of Bleeding from Esophageal Varices (Instructions for Use), C. R. Bard, Inc., Covington, GA, USA (1998).

Baron, et al., "Acute Necrotizing Pancreatitis", (1999) New England J. of Medicine, vol. 340, No. 18, pp. 1412-1417 (1999).

Batterham, et al., "Inhibition of Food Intake in Obese Subjects by Peptide YY3-36", New England J. Med., pp. 941-948 (Sep. 4, 2003).

Beglinger et al., "Postprandial Control of Gallbladder Contraction and Exocrine Pancreatic Secretion in Man", Euro. J. of Clinical Investigation, pp. 827-834 (1992).

Bell, et al., "The Interplay Between Hydrogen Ions, Bicarbonate Ions and Osmolality in the Anterior Duodenum Modulating Gastric Function in the Conscious Calf", J. Physiol., pp. 331-341 (1981).

Benini, "Gastric Emptying and Dyspeptic Symptoms in Patients with Gastroesophageal Reflux", Amer. J. of Gastroenterology, pp. 1351-1354 (1996).

Benini, et al., "Omeprazole Causes Delay in Gastric Emptying of Digestible Meals", Digestive Diseases and Sciences, pp. 469-474 (1996).

Berthoud et al., "Characteristics of Gastric and Pancreatic Reponses to Vagal Stimulation with Varied Frequencies: Evidence for Different Fiber Calibers?", J. Auto. Nervous Sys., pp. 77-84 (1987).

Biron, et al., "Clinical Experience with Biliopancreatic Bypass and Gastrectomy or Selective Vagotomy for Morbid Obesity", Canadian J. of Surg., vol. 29, No. 6, pp. 408-410 (1986).

Boss, et al., Laparoscopic Truncal Vagotomy for Severe Obesity: Six Month Experience in 10 Patients from a Prospective, Two-Center Study, Proceedings of the 24th Annual Meeting, American Society for Metabolic & Bariatric Surgery, Plenary Session Abstracts, (Abstract No. 44) (Jun. 2007) (reprinted from http://www.asbs.org/archive/abstracts/plenary_edited_2007.pdf).

Bourde, et al., "Vagal Stimulation: II. Its Effect on Pancreatic Secretion in Conscious Dogs", Annals of Surgery, pp. 357-364 (1970).

Burneo, et al., "Weight Loss Associated With Vagus Nerve Stimulation", Neurology, vol. 59, pp. 463-464 (Aug. (1 of 2) 2002).

Camilleri et al., "Determinants of Response to a Prokinetic Agent in Neuropathic Chronic Intestinal Motility Disorder", American Gastroenterological Association, vol. 106, No. 4, pp. 916-923 (1994).

Cann PA, et al. "Irritable Bowel Syndrome: Relationship of Disorders in the Transit of a Single Solid Meal to Symptoms Patterns", Gut, (1983);24:405-411.

Chang, et al., "Long-Term Results of Duodenectomy with Highly Selective Vagotomy in the Treatment of complicated Duodenal Ulcers", Amer. J. of Surg., vol. 181, pp. 372-376 (2001).

Chatzicostas, et al., "Balthazar computed tomography severity index is superior to Ranson criteria and APACHE II and III scoring systems in predicting acute pancreatitis outcome", J. Clinical Gastroenterology, 36(3), pp. 253-260 (2003).

Chey et al., "Neural Hormonal Regulation of Exocrine Pancreatic Secretion", Pancreatology, pp. 320-335 (2001).

Chey, "Regulation of Pancreatic Exocrine Secretion", Int'l J. of Pancreatology, pp. 7-20 (1991).

Cigaina, "Gastric Pacing As Therapy for Morbid Obesity", Obesity Surgery, vol. 12, Supplement, pp. 12S-16S (2002).

Coffin, et al, "Somatic Stimulation Reduces Perception of Gut Distention in Humans", Gastroenterology, vol. 107, pp. 1636-1642 (1994).

Cuomo R, et al., "Functional Dyspepsia Symptoms, Gastric Emptying and Satiety Provocation Test: Analysis of Relationships", Scand J Gastroenterol, (2001) 36:1030-1036.

Cyberonics, Inc. 2001 Annual Report, pp. 1, 5-7 and 16 (2001).

Cyberonics, Inc. 2003 Form 10-K to Securities and Exchange Commission, pp. 1 and 10 as printed on May 23, 2006 from http://www.secinfo.com/dsvRu.23yb.htm.

D'Argent, "Gastric Electrical Stimulation: Preliminary Results", *Obesity Surgery*, vol. 12, Supplement, pp. 21S-25S (2002).

Dapoigny et al., "Vagal influence on colonic motor activity in conscious nonhuman primates", *Am. J. Physiol.*, 262: G231-G236 (1992).

DeVault KR, et al., "Updated Guidelines for the Diagnosis and Treatment of Gastroesophageal Reflux Disease", *Am J Gastroenterol*, (1999);94:1434-1442.

Drossman, "Rome II: A Multinational Consensus Document on Gastrointestinal Disorders—The Functional Gastrointestinal Disorders and the Rome II Process", *Gut*, vol. 45 (Suppl II:II1-II5 (1999).

Easton, "The Nerve Impulse Seen From Outside", Florida State University, Department Jul. 2000 available on line at http://www.bio.fsu.edu/faculty-easton_actionpotential.htm (topics 1-35a) (72 pages).

Estevão-Costa et al., "Delayed Gastric Emptying and Gastroesophageal Reflux: A Pathophysiologic Relationship", J. of Pediatric Gastroenterology and Nutrition, pp. 471-474 (2001).

Evans PR, et al., "Gastroparesis and Small Bowel Dysmotility in Irritable Bowel Syndrome", *Dig Dis Sci* (1997);42:2087-2093.

Evans PR, et al., "Jejunal Sensorimotor Dysfunction in Irritable Bowel Syndrome: Clinical and Psychosocial Features", Gastroenterol, (1996);110:393-404.

Faris, et al., "Effect of Decreasing Afferent Vagal Activity with Ondansetron on Symptoms of Bulimia Nervosa: a Randomized, Double-Blind Trial", *The Lancet*, pp. 792-797 (2000).

Furukawa et al., "Effects of Selective Vagal Stimulation on the Gallbladder and Sphincter of Oddi and Peripheral Vagal Routes Mediating Bile Evacuative Responses Induced by Hypothalamic Stimulation", JJP vol. 42 321-334, (1992).

George, et al., "Vagus Nerve Stimulation Therapy", *Neurology*, vol. 59 (Suppl 4) pp. S56-S61 (2002).

Gershon, "The Second Brain", Harper Collins Publishers, Inc, New York, NY p. 19 (1998).

Görtz, et al., "A Five- to Eight-Year Follow-up Study of Truncal Vagotomy as a Treatment for Morbid Obesity", Proceedings of the Third Annual Meeting, American Society for Bariatric Surgery, p. 145 (1986) (Abstract).

Gortz, et al., "Truncal Vagotomy Reduces Food and Liquid Intake in Man", *Physiology & Behavior*, vol. 48, pp. 779-781 (1990).

Greydanus et al., "Neurohormonal Factors in Functional Dyspepsia: Insights on Pathophysiological Mechanisms", *American Gastroenterological Association*, vol. 100, No. 5, pp. 1311-1318 (1991).

Grossi, et al., "Swallows, Oesophageal and Gastric Motility in Normal Subjects and in Patients with Gastro-Oesophageal Reflux Disease: a 24-h pH-Manometric Study", Neurogastroenterology and Motility, pp. 115-121 (1998).

Guyton AC, et al., "Propulsion and Mixing of Food in the Alimentary Tract", Textbook of Medical Physiology, 10$^{th}$ ed. Philadelphia: W. B. Saunders and Company, 200:728-734.

Guyton AC, et al., "Secretory Functions of the Alimentary Tract", Textbook of Medical Physiology, 10$^{th}$ ed. Philadelphia: W. B. Saunders and Company, 200:738-753 (2000).

Hausken, et al., "Low Vagal Tone and Antral Dysmotility in Patients with Functional Dyspepsia", *Psychosomatic Medicine*, 55: 12-22 (1993).

Heitkemper, et al., "Evidence for Automatic Nervous System Imbalance in Women with Irritable Bowel Syndrome", *Digestive Diseases and* Sciences, vol. 43, No. 9, pp. 2093-2098 (1998).

Hjelland, et al., "Vagal tone and meal-induced abdominal symptoms in healthy subjects", *Digestion*, 65: 172-176 (2002).

Holst et al., "Nervous Control of Pancreatic Exocrine Secretion in Pigs", *Acta Physiol. Scand.*, vol. 105, pp. 33-51 (1979).

Holst et al "Nervous control of pancreatic endocrine secretion in pigs" *Acta Physiol Scand*, (1981), 111:1-7.

Hornbuckle K, et al. "The Diagnosis and Work-Up of the Patient with Gastroparesis", *J Clin Gastroenterol*, (2000);30:117-124.

Hunt, "The Relationship Between the Control of pH and Healing and Symptom Relief in Gastro-Oesophageal Reflux Disease", *Ailment Pharmacol Ther.*, 9 (Suppl. 1) pp. 3-7 (1995).

ICD-10, "Classification of Mental and Behavioural Disorders", World Health Organization (1992), 2 pages, printed from http://www.mental-health-matters.com/disorders/dis_details.

International Search Report (Partial) mailed Aug. 28, 2008.

International Search Report and Written Opinion mailed Jul. 8, 2009.

International Search Report and Written Opinion mailed Nov. 29, 2006.

Kaiser, "Gallstone Ileus", *New England J. of Medicine*, vol. 336, No. 12, pp. 879-880 (1997) (correspondence).

Kaminski et al., "The Effect of Electrical Vagal Stimulation on Canine Pancreatic Exocrine Function", Surgery, pp. 545-552 (1975).

Kellow JE, et al., "Dysmotility of the Small Intestine in Irritable Bowel Syndrome", *Gut* (1988);29:1236-1243.

Kellow JE, et al., "Rome II: A Multinational Consensus Document on Gastrointestinal Disorders—Principles of Applied Neurogastroenterology: Physiology/Motility-Sensation", *Gut*, (1999);45(Suppl II):II17-II24.

Kilgore, K. et al., "Nerve Conduction Block Utilising High-Frequency Alternating Current," *Medical & Biological Engineering & Computing*, vol. 42, pp. 394-406 (2004).

Koren et al., "Vagus Nerve Stimulation Does Not Lead to Significant Changes in Body Weight in Patients With Epilepsy", *Epilepsy & Behavior*, vol. 8, pp. 246-249 (2005).

Korner et al., "To Eat or Not to Eat—How the Gut Talks to the Brain", *New England J. Med.*, pp. 926-928 (Sep. 4, 2003).

Kosel, et al., "Beyond the Treatment of Epilepsy: New Applications of Vagus Nerve Stimulation in Psychiatry", *CNS Spectrums*, vol. 8, No. 7, pp. 515-521 (Jul. 2003).

Kral, "Vagotomy as a Treatment for Morbid Obesity", *Surg. Clinics of N. Amer.*, vol. 59, No. 6, pp. 1131-1138 (1979).

Kral, "Vagotomy for Treatment of Severe Obesity", *The Lancet*, pp. 307-308 (1978).

Kral, et al., "Gastroplasty for Obesity: Long-Term Weight Loss Improved by Vagotomy", *World J. Surg.*, vol. 17, pp. 75-79 (1993).

Lagergren J, et al., "Symptomatic Gastroesophageal Reflux as a Risk Factor for Esophageal Adenocarcinoma", *New Engl J Med*, (1999);340:825-829, 831.

Layer et al., "Human pancreatic secretion during phase II antral motility of the interdigestive cycle", *American Physiological Society*, 88 G249-G253 (1988).

Lin et al., "Hardware—software co-design of portable functional gastrointestinal stimulator system", *J. of Medical Eng. & Tech.*, vol. 27, No. 4 pp. 164-177 (2003).

Long, M.S. editor, Chapter 3, "The Stomach", Gastrointestinal System, 2$^{nd}$ Ed., Mosby Publisher, London (2002).

Long, M.S. editor, Chapter 4, "The Liver and Biliary Tract", Gastrointestinal System, 2$^{nd}$ Ed., Mosby Publisher, London (2002).

Mabayo, et al., "Inhibition of Food Passage by Osmeprazole in the Chicken", European J. of Pharmacology, pp. 161-165 (1995).

Martin-Portugues, et al., "Histopathologic Features of the Vagus Nerve After Electrical Stimulation in Swine", *Histol Histopathol*, vol. 20, pp. 851-856 (2005).

Medical Encyclopedia: Anorexia Nervosa, U.S. National Library of Medicine and National Institutes of Health, pp. 1-3 (Jun. 22, 2004) printed from http://www.nlm.nih.gov/medlineplus/print/ency/article/000362.htm, Jun. 6, 2006.

Merio R, et al., "Slow Gastric Emptying in Type 1 Diabetes: Relation to Autonomic and Peripheral Neuropathy, Blood Glucose, and Glycemic Control", *Diabetes Care*, (1997);20:419-423.

Mintchev, et al., "Electrogastrographic impact of multi-site functional gastric electrical stimulation", *J. of Medical Eng. & Tech.*, vol. 23, No. 1 pp. 5-9 (1999).

Mittal RK, et al., "Mechanism of Disease: The Esophagogastric Junction", *New Engl J Med*, (1997);336:924-927, 929-932.

Netter, "Atlas of Human Anatomy", 3rd Ed., Plate 120, (Icon Learning Systems, New Jersey) (2003).

Norton, et al., "Optimizing Outcomes in Acute Pancreatitis", *Drugs*, 61(11), pp. 1581-1591 (2001).

Novartis product description, Zelnorm®, Jul. 2002 (T2002-19).

O'Brien, P. et al., "The Laparoscopic Adjustable Gastric Band (Lap-Band®): A Prospective Study of Medium-Term Effects on Weight, Health and Quality of Life," *Obesity Surgery*, vol. 12 , pp. 652-660 (2002).

Owyang, "Negative Feedback Control of Exocrine Pancreatic Secretion: Role of Cholecystokinin and Cholinergic Pathway", Symposium: Physiology of Cholecystokinin, American Institute of Nutrition, pp. 1321S-1326S (1994).

Paterson CA, et al., "Determinants of Occurrence and Volume of Transpyloric Flow During Gastric Emptying of Liquids in Dogs: Importance of Vagal Input", Dig Dis Sci, (2000);45:1509-1516.

Peeters, et al., "Obesity in Adulthood and Its Consequences for Life Expectancy: A Life Table Analysis", Annals of Internal Medicine, vol. 138, No. 1, pp. 24-32 (2003).

Petrofsky, et al., "Impact of Recruitment Order on Electrode Design for Neural Prosthetics of Skeletal Muscle", Am. J. of Physical Medicine, vol. 60, No. 5, pp. 243-253 (1981).

Poelmans J, et al., "Prospective Study on the Incidence of Chronic Ear Complaints Related to Gastroesophageal Reflux and on the Outcome of Antireflux Therapy", Ann Otol Rhinol Laryngol, (2002);111:933-938.

Product Brochure, "ATROSTIM Phrenic Nerve Stimulator," AtroTech Oy, P.O. Box 28, FIN-33721 Tampere, Finland, 2 pages (Jun. 2004).

Rashev et al., "Microprocessor-Controlled Colonic Peristalsis", Digestive Diseases and Sciences, vol. 47, No. 5, pp. 1034-1048 (2002).

Rashev, et al., "Three-dimensional static parametric modelling of phasic colonic contractions for the purpose of microprocessor-controlled functional stimulation", J. of Medical Eng. & Tech., vol. 25, No. 3 pp. 85-96 (2001).

Rasmussen, et al., "A Double-Blind Placebo-Controlled Study on the Effects of Omeprazole on Gut Hormone Secretion and Gastric Emptying Rate", Scand. J. Gastroenterol, pp. 900-905 (1997).

Rösch et al., "Frequency-Dependent Secretion of Pancreatic Amylase, Lipase, Trypsin, and Chymotrypsin During Vagal Stimulation in Rats", Pancreas, pp. 499-506 (1990).

Roslin et al., "The Use of Electrical Stimulation of the Vagus Nerve to Treat Morbid Obesity", Epilepsy & Behavior, vol. 2, S11-S16 (2001) at p. S13.

Roslin, et al., "Vagus Nerve Stimulation in the Treatment of Morbid Obesity", Ch. 6 to Vagus Nerve Stimulation, 2nd Ed., pp. 113-121 (Schlachter et al. ed., Martin Dunitz), 2003.

Sarnelli G, et al., "Symptoms Associated with Impaired Gastric Emptying of Solids and Liquids in Functional Dyspepsia", Am J Gastroenterol, (2003) 98:783-788.

Schapiro, et al., "Neurohypophyseal Regulation of the Exocrine Pancreas", Amer. J. of Gastroenterology, pp. 587-591 (1979).

Scheffer RC, et al., "Elicitation of Transient Lower Oesophageal Sphincter Relaxations in Response to Gastric Distension", Neurogastroenterol Motil, (2002);14:647-651, 654.

Schmidt T, et al., "Ambulatory 24-Hour Jejunal Motility in Diarrhea-Predominant Irritable Bowel Syndrome", J Gastroenterol, (1996);31:581-584, 586-589.

Schwartz MP, et al., "Chemospecific Alterations in Duodenal Perception and Motor Response in Functional Dyspepsia", Am J Gastroenterol, (2001);96:2596-2602.

Schwartz MP, et al., "Human Duodenal Motor Activity in Response to Acid and Different Nutrients", Dig Dis Sci, (2001);46:1472-1481.

Shikora, "'What are the Yanks Doing' The U.S. Experience with Implantable Gastric Stimulation (IGS) for the Treatment of Obesity—Update on the Ongoing Clinical Trials", Obesity Surgery, vol. 14, Supplement, S40-S48 (2004).

Simren M, et al., "Abnormal Propagation Pattern of Duodenal Pressure Waves in the Irritable Bowel Syndrome (IBS)", Dig Dis Sci, (2000);45:2151-2159, 2161.

Smith, et al., "Truncal Vagotomy in Hypothalamic Obesity", The Lancet, pp. 1330-1331 (1983).

Solomonow, et al., "Control of Muscle Contractile Force through Indirect High-Frequency Stimulation", Am. J. of Physical Medicine, vol. 62, No. 2, pp. 71-82 (1983).

Sontag SJ, et al., "Asthmatics with Gastroesophageal Reflux: Long Term Results of a Randomized Trial of Medical and Surgical Antireflux Therapies", Am J Gastroenterol, (2003);98:987-999.

Soran, et al., "Outcome and quality of life of patients with acute pancreatitis requiring intensive care", J. Surg. Res., 91(1), pp. 89-94 (2000).

Stanghellini V, et al., "Risk Indicators of Delayed Gastric Emptying of Solids in Patients with Functional Dyspepsia", Gastroenterol, (1996) 110:1036-1042.

Steer et al., "Chronic Pancreatitis", New England J. of Medicine, pp. 1482-1490 (1995).

Steinbrook, "An Opioid Antagonist for Postoperative Ileus", New England J. of Medicine, vol. 345, No. 13, pp. 988-989 (2001) (Editorial).

Steinbrook, R., "Surgery for Severe Obesity", New England J. Med., vol. 350, pp. 1075-1079 (2004).

Tack J, et al., "Role of Impaired Gastric Accommodation to a Meal in Functional Dyspepsia", Gastroenterol, (1998) 115:1346-1352.

Tack J, et al., "Symptom Pattern and Gastric Emptying Rate Assessed by the Octanoic Acid Breath Test in Functional Dyspepsia" [abstract]. Gastroenterol, (1998) 114:A301.

Taguchi, et al., "Selective Postoperative Inhibition of Gastrointestinal Opioid Receptors", New England J. of Medicine, vol. 345, No. 13, pp. 935-940 (2001).

Talley et al., "Rome II: A Multinational Consensus Document on Gastrointestinal Disorders—Functional Gastroduodenal Disorders" Gut, vol. 45 (Suppl II), pp. II37-II42 (1999).

Taylor, et al., "Effects of Pancreatic Polypeptide, Caerulein, and Bombesin on Satiety in Obese Mice", American Journal of Physiology, 248:G277-G280 (1985).

Thompson WG, et al., "Rome II: A Multinational Consensus Document on Gastrointestinal Disorders—Functional Bowel Disorders and Functional Abdominal Pain", Gut, (1999) ;45(Suppl II):II43-II47.

Tiscornia et al., "Neural Control of the Exocrine Pancreas: An Analysis of the Cholinergic, Adrenergic, and Peptidergic Pathways and Their Positive and Negative Components 1: Neural Mechanisms", Mount Sinai J. of Medicine, pp. 366-383 (1987).

Tougas, "The Autonomic Nervous System in Functional Bowel Disorders", Gut, vol. 47 (Suppl IV), pp. iv78-iv80 (2000).

Tzu-Ming, et al., "Long-Term Results of Duodenectomy with Highly Selective Vagotomy in the Treatment of complicated Duodenal Ulcers", Amer. J. of Surg., vol. 181, pp. 372-376 (2001).

Undeland KA, et al., "Wide Gastric Antrum and Low Vagal Tone in Patients with Diabetes Mellitus Type 1 Compared to Patients with Functional Dyspepsia and Healthy Individuals", Dig Dis Sci, (1996) 41:9-16.

U.S. Appl. No. 10/674,330, Office Action mailed Apr. 22, 2008.

U.S. Appl. No. 11/040,767, Notice of Allowance dated Jun. 22, 2009.

U.S. Appl. No. 11/656,122, Notice of Allowance dated Aug. 7, 2009.

U.S. Appl. No. 11/891,770, Office Action dated Jul. 20, 2009.

Van Den Honert, et al., "Generation of Unidirectionally Propagated Action Potentials in a Peripheral Nerve by Brief Stimuli", Science, vol. 206, pp. 1311-1312 (1979).

Van Wijk HJ, et al., "Gastric Emptying and Dyspeptic Symptoms in the Irritable Bowel Syndrome", Scand J Gastroenterol, (1992);27:99-100, 101.

Vassallo MJ, et al., "Colonic Tone and Motility in Patients with Irritable Bowel Syndrome", Mayo Clin Proc, (1992);67:725-727, 729-731.

Wilmer A, et al., "Ambulatory Gastrojejunal Manometry in Severe Motility-like Dyspepsia: Lack of Correlation between Dysmotility, Symptoms and Gastric Emptying", Gut, (1998) 42:235-242.

Yoshinaga, et al., "Cholecystokinin Acts as an Essential Factor in the Exacerbation of Pancreatic Bile Duct Ligation-Induced Rat Pancreatitis Model Under Non-Fasting Condition", Japanese J. Pharmacol, vol. 84, pp. 44-50 (2000).

Zapater, et al., "Do Muscarinic Receptors Play a Role in Acute Pancreatitis?", Clin. Drug Invest., 20(6), pp. 401-408 (2000).

Camilleri, M. et al., "Vagal Blocking for Obesity Control (Vbloc): Plasma Pancreatic Polypeptide (PPP) Response to a Standardized Sham Meal Challenge," Obesity, vol. 15, Supplement, Abstract No. 20-OR, pp. A6-A7 (Sep. 2007).

Toouli, J. et al., "Vagal blocking for obesity control (VBLOC): Effects on excess weight loss, calorie intake, satiation and satiety," Obesity Surgery, vol. 17, Abstract No. 83, p. 1043 (2007).

Tweden, K. et al., "Vagal Blocking for Obesity Control (VBLOC): Concordance of Effects of Very High Frequency Blocking Current at the Neural and Organ Levels Using Two Preclinical Models," Gastroenterology, vol. 130, No. 4, Suppl. 2, Abstract No. 951, p. A-148 (Apr. 2006).

Tweden et al., Obesity Surgery (2006) 16:988.

* cited by examiner

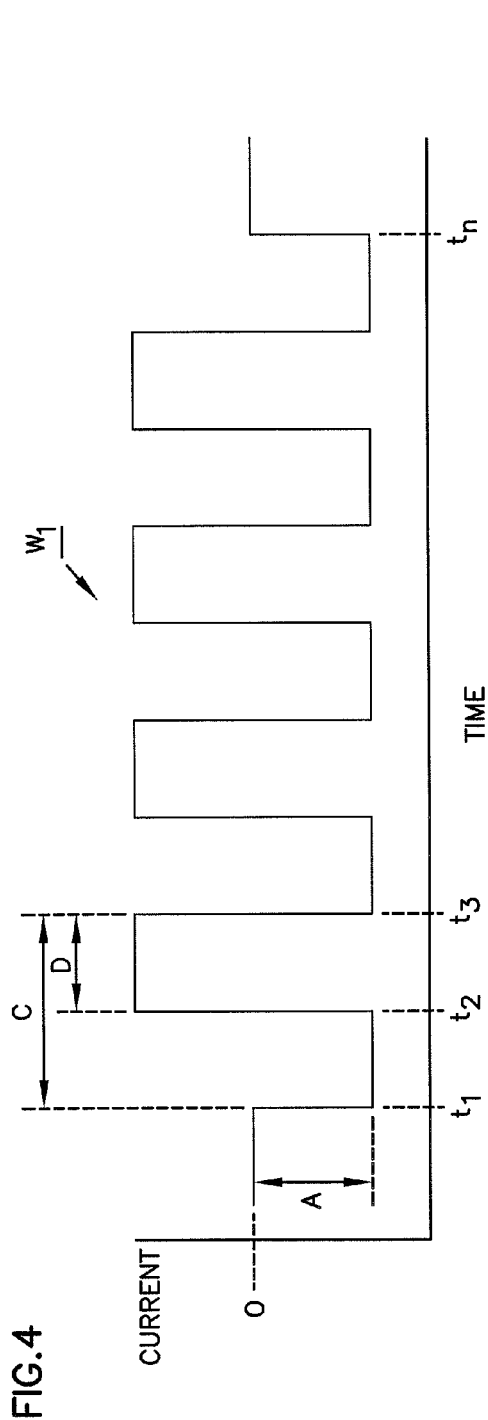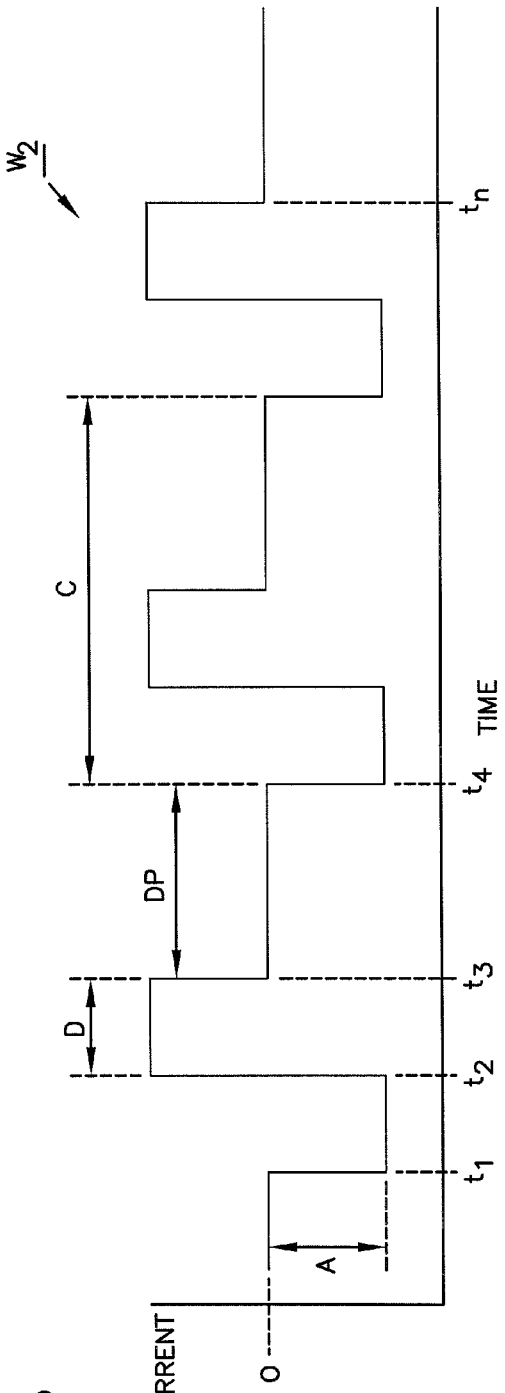

NEURAL ELECTRODE TREATMENT

CROSS REFERENCE TO RELATED APPLICATION

This application is a continuation of U.S. patent application No. 11/205,415, filed Aug. 17, 2005, now U.S. Pat. No. 7,672,727, which application is incorporated herein by reference.

I. BACKGROUND OF THE INVENTION

1. Field of the Invention

This invention pertains to electrodes for nerves and therapeutic signals to be applied to such electrodes. More particularly, this invention pertains to such electrodes and signals for placement on the vagus nerve for treatment of obesity.

2. Prior Art a. Neural Conduction Block

The Assignee of the present application has a number of pending U.S. patent applications pertaining to application of a conduction block technology to a nerve for a treatment of a variety of disorders. These applications include the following (all filed Sep. 29, 2003): U.S. patent application Ser. No. 10/674,330, which issued as U.S. Pat. No. 7,489,969 (published Sep. 2, 2004 as Publication No. US 2004/0172086 A1); U.S. patent application Ser. No. 10/675,818 (published Sep. 9, 2004 as US Patent Application Publication No. US 2004/0176812 A1), now abandoned, and U.S. patent application Ser. No. 10/674,324 (published Sep. 2, 2004 as US Patent Application Publication No. 2004/0172085 A1), now abandoned. These patent applications describe, in a preferred embodiment, the application of neural conduction block therapy to a vagus nerve alone or in combination with a stimulation of the nerve.

The conduction block therapy includes application of an electrical signal with parameters selected to down-regulate vagal activity by creating conditions in which normal nerve propagation potentials are blocked at the application of the signal on both afferent and efferent nerves fibers of the vagus. A number of different disorders are identified for treatment through the technique. These disorders include obesity, pancreatitis and other gastrointestinal disorders such as irritable bowel syndrome and functional disorders.

Electrodes may be placed directly on the vagus (for example as cuff electrodes) or may be placed on bands surrounding the vagus at the esophagus or placed on an intraluminal device within the esophagus for transmitting the energy from the device across the tissue of the esophagus to the vagus nerves in the region of the esophagus. These embodiments are disclosed with greater particularity in the Assignee's U.S. patent application Ser. No. 10/752,944, which has issued as U.S. Pat. No. 7,167,750, and Ser. No. 10/752,940, which issued as U.S. Pat. No. 7,444,183, both filed Jan. 6, 2004 with respective publication dates of Aug. 26, 2004 and Sep. 2, 2004, Publication Nos. US 2004/0167583 A1 and 2004/0172088 A1.

b. Blocking Signal Parameters and Duty Cycle

On Jun. 30, 2004 the Assignee of the present application filed Ser. No. 10/881,045 (published Feb. 17, 2005 as Publication No. US 2005/0038484 A1), which issued as U.S. Pat. No. 7,844,338, noting that a duty cycle of electrical impulses to the nerve to block neural conduction on the nerve can be adjusted between periods of blocking and no blocking in order to vary the amount of down regulation of the vagus nerve as well as preventing accommodation by the enteric nervous system.

On Jan. 21, 2005 the Assignee filed Ser. No. 11/040,767, which issued as U.S. Pat. No. 7,613,515, describing with greater particularity parameters for controlling block and to avoid accommodation. That application notes that a representative blocking signal is preferably greater than 500 Hz and that such conduction block is preferably within the parameters disclosed in Solomonow, et al. "control of muscle contractile force through indirect high-frequency stimulation", American Journal of Physical Medicine, Volume 62, No. 2, pages 71-82 (1983). Particularly, the nerve conduction block is applied with electrical signals selected to block the entire cross-section of the nerve (for example, both afferent, efferent, myelinated and non-myelinated fibers) at the site of applying the blocking signal (as opposed to selected subgroups of nerve fibers or just afferent and not efferent or vice versa).

Preferably, the frequency of the blocking signal is selected to exceed a 200 Hz threshold frequency described in Solomonow, et al. More preferred parameters are a frequency in excess of 500 Hz (with other parameters as non-limiting examples, being an amplitude of 1-8 mA, pulse width of 100 microseconds, and a duty cycle of 5 minutes on and 5 minutes off. A more preferred blocking signal has a frequency of 3,000 Hz to 5,000 Hz or greater applied by either by bi-polar or mono-polar electrodes. Such a signal has a preferred pulse width of 100 micro-seconds (associated with a frequency of 5,000 Hz).

It is believed this frequency and pulse width best avoid neural recovery from blocking and avoid re-polarization of a nerve. A "short-off" time in the pulse cycle (for example, between cycles or within a cycle) can be acceptable as long as it is short enough to avoid nerve re-polarization. The waveform may be a square, triangular or sinusoidal waveform or other shape. The higher frequencies of 5,000 Hz or more have been found, in porcine studies, to result in more consistent neural conduction block. Kilgore, et al., "Nerve Conduction Block Utilizing High-Frequency Alternating Current", *Medical and Biological Engineering and Computing*, Vol. 24, pp. 394-406 (2004). Applicants have determined that a signal amplitude of 0.5 mA to 8 mA is adequate for blocking. However, other amplitudes may suffice.

While a duty cycle can be a predetermined time period, it is currently preferred that the duty cycle be less fixed to reduce the likelihood of patient accommodation whereby the autonomic (parasympathetic, sympathetic and enteric) and/or the central nervous systems accommodates for the loss of signals on the vagus or other nerve. While the periods of off and on can be stable or random, they can be set at any fixed or non-fixed sequence (for example, 5 minutes on followed by 5 minutes off repeated for the duration of the therapy or, alternatively, 5 minutes on followed by 10 minutes off as a first cycle with a following cycle meaning a different set of time—such as 10 minutes on and 2 minutes off, with a non-repeating duty cycle continuing over a 24 hour period). Other signal attributes can be varied to reduce the likelihood of accommodation by the nerve or an organ. These include altering the power, waveform or pulse width.

II. SUMMARY OF THE INVENTION

According to a preferred embodiment of the present invention, an apparatus is disclosed for applying a signal to a nerve for the treatment of a disorder. The apparatus includes a first electrode and a second electrode. Each of the electrodes is adapted to be secured to a nerve of a patient. A signal generator is electrically connected to each of the first and second electrodes. The signal generator is adapted to create a signal having a first waveform at the first electrode and a second waveform at the second electrode. The waveforms have parameters selected to block propagation of neural action potentials. The waveforms have a repeating pattern of cycles of pulses with a delay period between at least selected ones of said pulses. In one embodiment, the first and second waveforms are out of phase for a cycle of one of the waveforms to occur during a delay period of the other of the waveforms.

III. BRIEF DESCRIPTION OF THE DRAWINGS

FIG. 4 is a graphical presentation of a waveform applied to a nerve with no delay between pulse cycles;

FIG. 5 is a graphical presentation of a waveform applied to a nerve with a delay between pulse cycles;

IV. DESCRIPTION OF THE PREFERRED EMBODIMENT

With reference now to the various drawing figures in which identical elements are numbered identically throughout, a description of the preferred embodiment of the present invention will now be provided. The present invention will be described with reference to placing electrodes contacts on both the anterior and posterior vagus nerves overlying the esophagus between a diaphragm and a stomach of a patient for the treatment of obesity. It will be appreciated this is a currently preferred embodiment and the present invention has wider applications as will be apparent to those skilled in the art and can be applied to other cranial nerves (such as the vagus) or peripheral nerves.

Further, while the preferred embodiment illustrates application of a signal to block the propagation of action potentials along a nerve, the present invention is applicable to signals to stimulate a nerve, inhibit nerve function or only partially block a nerve.

1. Alternative Electrode Configurations

Figure 3:
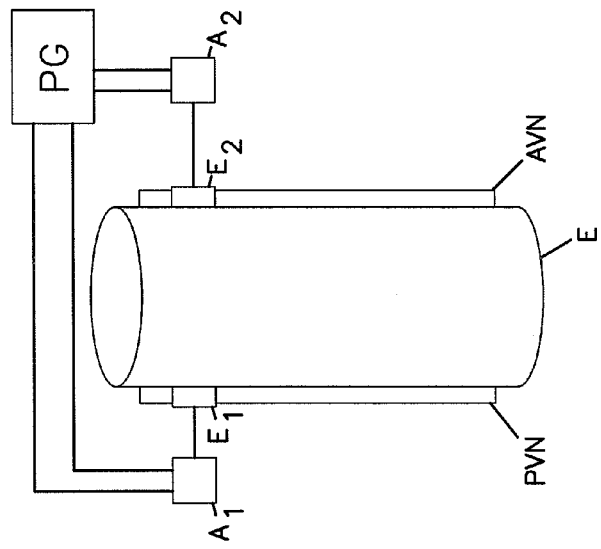
FIG. 3 is a view similar to FIG. 2 showing the anodic electrodes off of the nerves.
Figure 2:
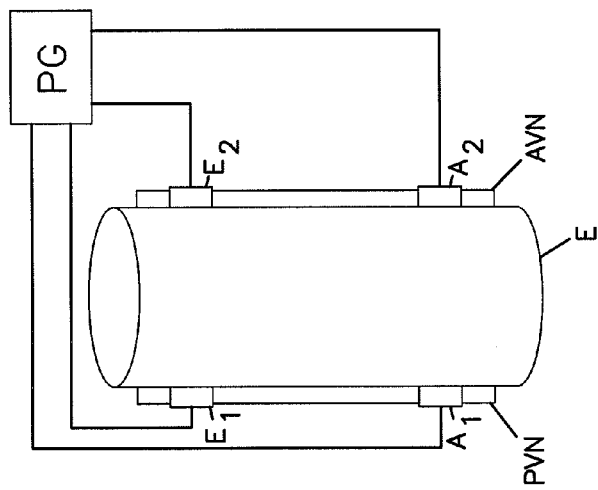
FIG. 2 is a view similar to FIG. 1 showing additional anodic electrodes on nerves.
Figure 1:
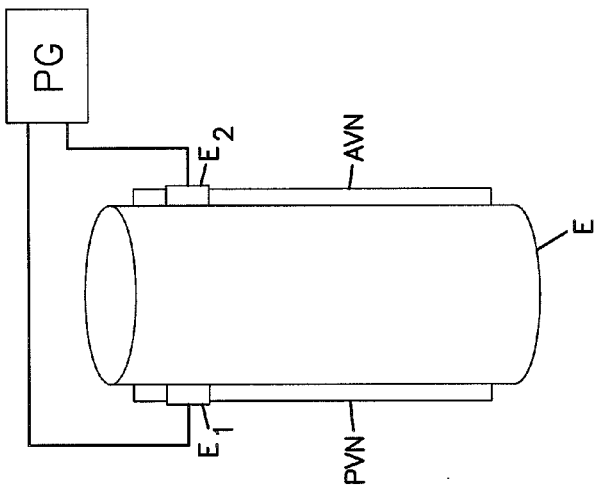
FIG. 1 is a schematic representation of electrodes on anterior and posterior vagus nerves on an esophagus.

FIGS. 1-3 illustrate alternative applications for applying a neural conduction block signal to vagus nerves in a preferred embodiment for the treatment of obesity. Such a signal downregulates a level of vagal activity and simulates, at least partially, a vagotomy that is reversible.

In FIGS. 1-3, the posterior vagus nerve PVN and the anterior vagus nerve AVN are shown extending along a length of the esophagus E and generally on diametrically opposite sides of the esophagus E just below the patient's diaphragm (not shown).

In each of FIGS. 1-3, a first electrode $E_1$ is placed on the posterior vagus nerve PVN. A second electrode $E_2$ is shown placed on the anterior vagus nerve AVN. The electrodes $E_1$, $E_2$ may be any suitable electrode for applying an electrical signal to a nerve. The electrodes $E_1$, $E_2$ could be cuff electrodes, patch electrodes, band electrodes or transluminal electrodes. The prior art contains numerous examples of electrodes for placement on nerves and treatments for applying electrical signals to such nerves. For example, U.S. Pat. No. 4,979,511 to Terry, Jr. dated Dec. 25, 1990 teaches an electrode on a helical silicone rubber coil for placement on a cervical vagus nerve for treatment of epilepsy. Also, U.S. Pat. No. 5,215,089 to Baker, Jr. issued Jun. 1, 1993 teaches an electrode for placement on a vagus and U.S. Pat. No. 5,251,634 to Weinberg issued Oct. 12, 1993 and U.S. Pat. No. 5,531,778 to Maschino et al. issued Jul. 2, 1996 and U.S. Pat. No. 6,600,956 to Maschino et al. issued Jul. 29, 2003 teach vagal electrodes.

Other techniques are known for applying signals directly to a nerve. These include patches placed over the nerve with electrodes on the patch positioned to overly the nerves. In so-called cuff electrodes, a portion of a nerve is dissected to permit a cuff to completely or partially encircle the nerve. An additional optional electrode format is such as that shown in a product brochure called "ATROSTIM Phrenic Nerve Stimulator", AtroTech Oy, P.O. Box 28, Fin-33721, Tampere, Finland (June 2004). The ATROSTIM nerve stimulator includes electrodes on opposite sides of PTFE strips for placement on opposite sides of a phrenic nerve for quad-polar stimulation. Another phrenic nerve electrode is sold by Avery Laboratories, Inc., 61 Mall Drive, Commack, N.Y., USA. The use of the Avery electrode is described in the website of Avery Laboratories, Inc. at breathingpacemakers.com.

The electrodes $E_1$, $E_2$ are connected by conductors to a pulse generator PG. The pulse generator PG may be a fully implanted unit containing a power source such as batteries or rechargeable batteries, or the like as well as processing controllers for maintaining a desired wave form and duty cycle on the electrodes $E_1$, $E_2$. Also, and as described in the Assignee's earlier described applications, the electrodes $E_1$, $E_2$ can be connected to an implanted antenna for receiving transdermal signals from an external controller transmitted across the patient's skin to the electrode through radio frequency signals. In this later embodiment, the pulse generator PG includes both implanted and external components.

FIG. 1 shows an arrangement for applying a uni-polar waveform to the nerves PVN, AVN. The current flow path between the electrodes $E_1$, $E_2$ flows through the esophagus.

The arrangement of FIG. 1 is uni-polar meaning there is only one location on the nerve subject to the treatment. In the embodiment of FIG. 1, the electrical signal is applied across the anterior vagus AVN and the posterior vagus PVN at electrodes $E_1$ and $E_2$.

FIG. 2 illustrates an alternative embodiment where each of the electrodes $E_1$ and $E_2$ has an associated anode electrode $A_1$, $A_2$. The anode electrodes $A_1$, $A_2$ are shown in FIG. 2 as being applied to the anterior vagus AVN and the posterior vagus PVN and spaced from electrodes $E_1$ and $E_2$. This results in bi-polar pacing (two sites per nerve receiving an electrical treatment). Unlike FIG. 1, the arrangement of FIG. 2 reduces likelihood of current flow through the esophagus thereby minimizing likelihood of patient sensation to the treatment.

FIG. 3 shows electrodes $A_1$, $A_2$ placed on other structures in generally close proximity (for example, 5 cm) of the primary electrodes $E_1$, $E_2$. These electrodes $A_1$, $A_2$ could be placed on the stomach, on the esophagus or on other anatomical structures in the general vicinity of the electrodes $E_1$, $E_2$. This results in uni-polar pacing similar to FIG. 1 but with the benefit of FIG. 2 in that current flow is not through the esophagus. Further, placement of the anode electrodes on the stomach permits monitoring of stomach contractions (e.g., by strain receptors associated with the anode electrodes) which can be of further benefit as will be described.

With the arrangement of FIG. 3, the pulse generator PG can be programmed to cancel the effect of the anode electrodes such that even though the anode electrodes are physically present, the effective circuit on the esophagus is that of FIG. 1. This adds greater flexibility to function of the apparatus as will be described.

In a preferred embodiment for treating obesity, the electrode configuration is that of FIG. 3 with the pulse generator PG programmed to permit functionally shifting to the configuration of FIG. 1. In the mode of FIG. 3 (with functioning anode electrode), the current path on the posterior nerve PVN is between the posterior nerve PVN and the anode $A_1$. Similarly, in such mode, the current path on the anterior nerve AVN is between the posterior nerve PVN and the anode $A_2$. With the apparatus of FIG. 3 in the functional mode of FIG. 1, the current path is between the anterior vagus nerve AVN and the posterior vagus nerve PVN.

2. Nerve-to-Nerve Waveform a. Continuous Waveform Without Delays Between Pulses

FIG. 4 shows a representative waveform $W_1$ of a signal applied across the electrodes $E_1$, $E_2$ of the arrangement of FIG. 1 (or in the arrangement of FIG. 3 controlled by the pulse generator to function in the mode of FIG. 1) showing current flow to the electrodes. The waveform $W_1$ is shown as a square waveform having an amplitude A and a pulse duration of D.

In a preferred embodiment, the amplitude A is preferably between 0.5 mA and 8 mA and more preferably about 4-6 mA. The duration D is, in a preferred embodiment, about 100 microseconds for the total cycle time C (i.e., the time between the initial application of the cycle at $t_1$ and the end of the cycle $t_3$) resulting in a frequency for the cycle of 5,000 Hz. A 100-microsecond pulse duration D for a 5,000 Hz signal results in no time between pulses where there is no signal. Longer pulse durations can be associated with lower frequencies. For example, a 200-microsecond pulse duration and a 2500 Hz frequency signal are also effective blocking signals. Still lower frequency signals are possible for effective blocking. However, it is believed a maximum pulse duration of 1 millisecond with an associated maximum frequency of 500 Hz represents an effective maximum pulse duration to avoid nerve recovery in most patients. A 200 Hz signal as suggested by Solomonow, et al., may still effect a blocking of a nerve.

The cycles of FIG. 4 are continuously repeating without substantial periods of dead time between cycles. Other than a potential for a few microseconds, there is no substantial period of time between the cycles where no current is applied to the electrodes. After some period of time (for example, 5 minutes), at time $t_n$, the signal may be stopped so that there is a period of off time in the duty cycle (for example 10 minutes).

b. Continuous Waveform With Delays Between Pulses

FIG. 5 shows an alternative waveform $W_2$. While similar to the waveform $W_1$ of FIG. 4, the waveform $W_2$ of FIG. 5 includes built-in delay periods DP (for example, the time period between time $t_3$ and $t_4$) between each cycle. By building into the waveform periods DP of no signal, power can be conserved. Where the duration of the delay period DP is 100 microseconds, in FIG. 5, the frequency of the cycle C (less the delay period DP) remains 5,000 Hz. Where the delay is 200 microseconds, the frequency of the cycle C is 2,500 Hz. The time delay DP (i.e., the time between $t_3$ and $t_4$) is selected to be shorter than a time delay which would otherwise permit recovery of the nerve.

3. Nerve to Anodic Electrodes Waveforms

Figure 6:
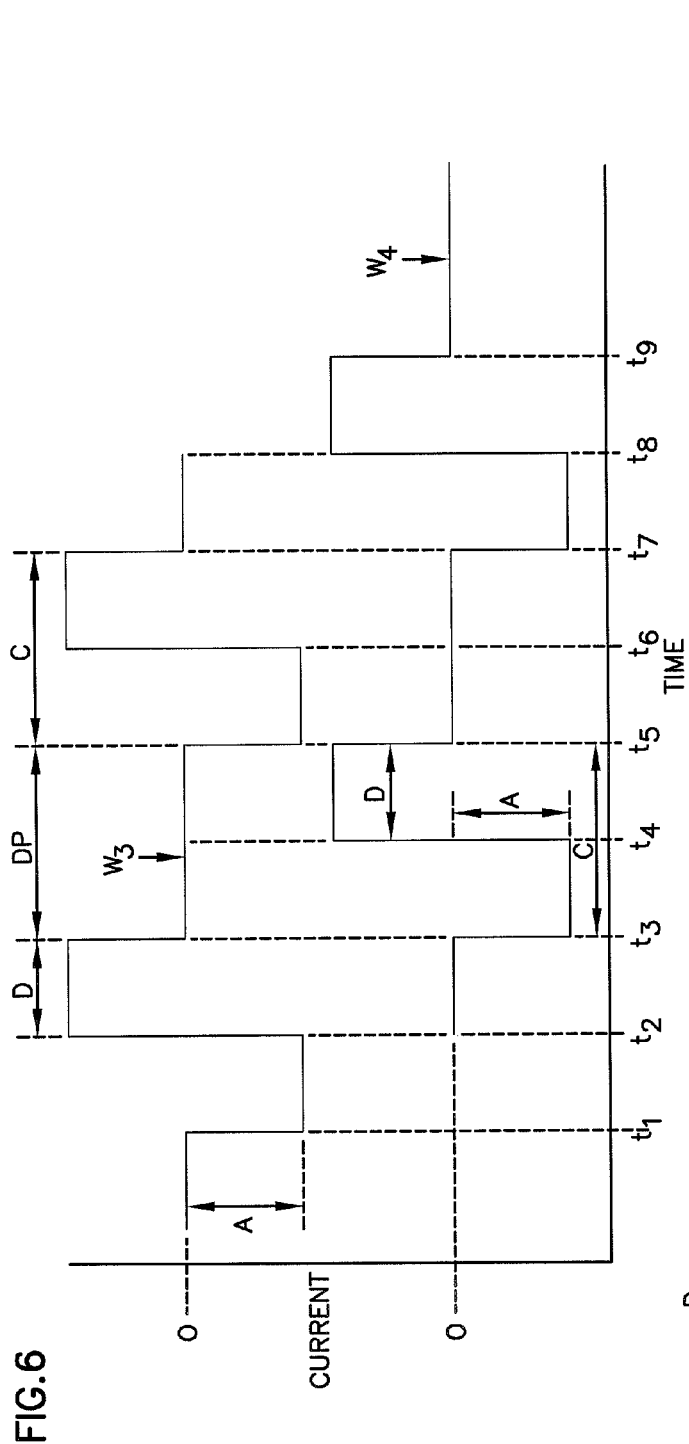
FIG. 6 is a graphical presentation of waveforms applied to two nerves with a delay between pulse cycles and with the timing of the waveforms offset.

FIG. 6 is a graphical representation of waveforms $W_3$, $W_4$ of signals applied to the electrodes $E_1$, $E_2$ in FIG. 3 in the mode of FIG. 3 with anodic electrodes. The upper waveform $W_3$ is the signal applied to electrode pairs $E_1$, $A_1$ and the lower waveform $W_4$ illustrates a signal applied to electrodes $E_2$, $A_2$.

Both waveforms $W_3$, $W_4$ are structurally identical having common amplitude A and pulse duration D with the same parameters, in a preferred embodiment, as described with reference to FIGS. 4 and 5. Also, the structure of both waveforms $W_3$, $W_4$ is similar to that of FIG. 5 in that the waveforms $W_3$, $W_4$ include a delay period DP between cycles in the waveforms $W_3$, $W_4$. In FIG. 6, the delay periods DP could be eliminated with both waveforms then resembling the waveform of FIG. 4.

It will be noted that the two waveforms $W_3$, $W_4$ are out of phase such that the pulse cycle C of one waveform is timed to be occurring during the delay period DP of the other waveform. Further, the delay period DP of a waveform is selected to equal the cycle time C of the other waveform (i.e., twice the pulse duration D). This length of delay period DP is the smallest preferred delay period DP since it results in avoiding an instance where both electrodes $E_1$, $E_2$ are energized which could result in a direct-current component between the electrodes $E_1$, $E_2$. A longer delay period DP could be applied when the delay period length is selected so that the two waveforms continue to avoid having periods of time where both electrodes $E_1$, $E_2$ are receiving a signal simultaneously. The maximum duration of the delay period DP is selected to be less than an amount of time which would otherwise permit the nerve to recover from the blocking signal.

The application of anode $A_1$, $A_2$ is similar to a so-called VDD lead used in cardiac pacing. An example of a VDD electrode is the Solox™ single-lead VDD electrode of Biotronik GmbH & Co., Woermannkehre 1, D-12359 Berlin, Germany. More information is provided at its website biotronik.com. The pacing tip of such electrode in placed in the right ventricle of a heart at the apex and the anode ring resides in the right ventricle.

4. Waveforms with Duty Cycles

FIG. 5 illustrates a waveform with very small delay periods. Substantially longer delay periods can be applied to a treatment. In such longer delay periods, a nerve may at least partially recover.

In rat studies performed for the assignee, applicants applied blocking signals as described to isolated sciatic nerves of rats. After an effective block was applied and turned off, the nerve recovered in about 10 minutes. In this context, recovery means the nerve response to a stimulus was substantially the same as a baseline response before application of the blocking signal. After about 2.5 minutes, the nerve had recovered about 50% of baseline. Also, the duty cycle can be turned completely off for extended period of times. For example, duty cycle could be applied for a 12-hour period associated with daytime and be continually off with a 12-hour period associated with the evening or during sleep hours.

Figure 7:
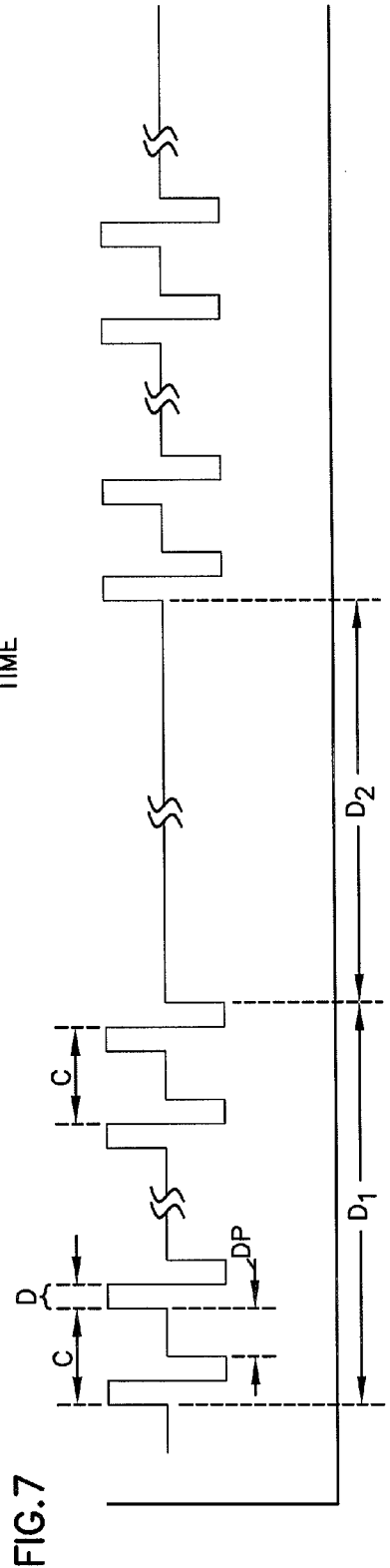
FIG. 7 is a graphical presentation of a waveform applied to a nerve with a delay between pulse cycles and with a long period of no signal to illustrate a duty cycle over time.

FIG. 7 illustrates a representative duty cycle applied to the waveform of FIG. 5 (i.e., a waveform with built-in small delay periods DP during which the nerve does not recover). It will be appreciated a similar duty cycle can be employed in the waveforms of FIGS. 4 and 6.

In FIG. 7, a plurality of cycles C such as that shown in FIG. 5 are shown in sequence for a duration $D_1$ of pulse application (either a blocking signal as previously described or a neural stimulation signal). The period of time may be two to five minutes to ensure an effective application of the signal is applied to a nerve. For application of a blocking signal, an effective application of the signal is estimated as about one minute and preferably 2 to 5 minutes to ensure the nerve has been treated to block propagation of action potentials along the nerve (as well as achieving desired end-organ response).

Followed by the pulse duration $D_1$, a period $D_2$ of no treatment for "off" portion of a duty cycle is shown which may last for 5 to 10 minutes associated with an estimate for an amount of time for the nerve to recover. After the off period, a sequence can repeat in identical format. The times of the pulse signal and the off signal may be varied to avoid nerve accommodation. Also, as previously stated, the duty cycle may include extended periods of off-time associated with sleeping or other periods during the day. The "off" period of 5 to 10 minutes avoids nerve accommodation while avoiding complete nerve recovery thereby maintaining therapy efficacy.

5. Programmable Options

As previously noted, the programmable pulse generator PG of FIG. 3 can be altered so that the electrodes on the nerves AVN, PVN can function as the functional equivalent of either of FIG. 1 or 3. Further, the pulse generator PG permits selection of any of the waveforms described above as well as altering pulse duration D, amplitude, delay periods DP and duty cycle.

6. Selection of Waveform Parameters

Effective blocking of neural impulses requires treating the nerve with a signal to prevent the depolarization of the nerve that is associated with the conduction of nerve signals (nerve action potentials) past the point of application of the blocking signal. As noted in the assignee's earlier applications (referenced above and incorporated by reference), such depolarization can be achieved by a direct current signal. However, such a signal represents a significant burden to a battery. Low frequency alternating current signals (e.g., less than 20 Hz) permit the nerve to recover. As a result, such signals are useful for stimulating therapies where the nerve is used as a highway for directing the stimulation signal to an organ. Where, as in the present application, the desired therapy is to block the nerve and prevent transmission of neural impulses along the nerve, a higher frequency maintains the nerve in a polarized state. As mentioned above with respect to articles of Solomonow et al. and Kilgore, et al. such frequencies are in excess of 200 Hz and up to 5,000 Hz or more.

Figure 18:
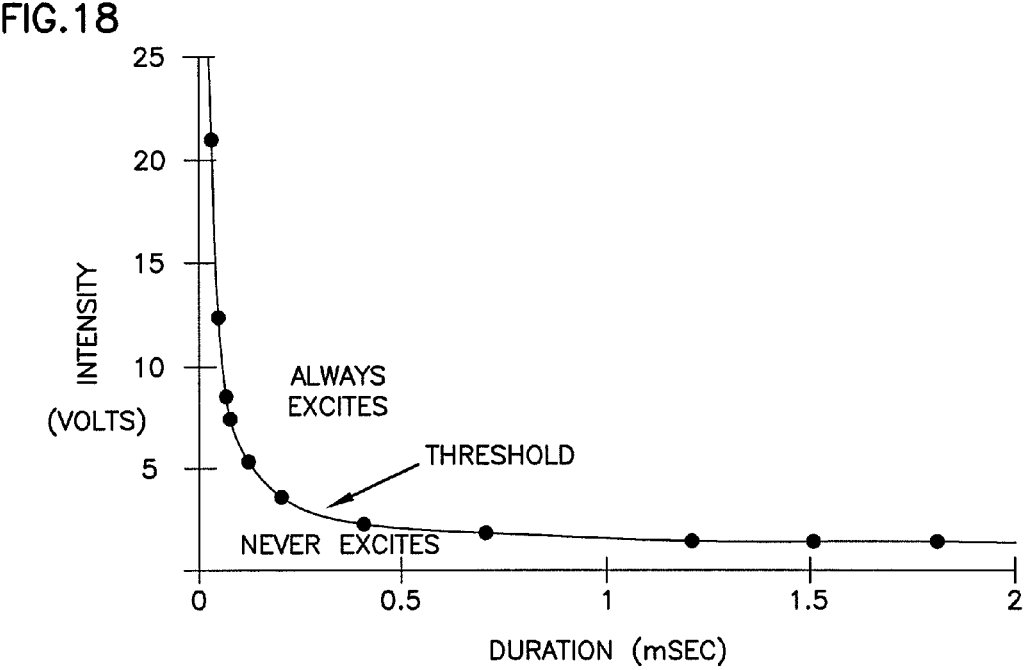
FIG. 18 is a strength-duration curve illustrating a threshold curve for effective neural blockage.

Effective blockage of a nerve is a function of both the strength of the signal applied to the nerve as well as the duration of such application. FIG. 18 illustrates such a relation. The curve of FIG. 18 is taken from Easton, "The Nerve Impulse Seen From Outside", Florida State University, Department of Biological Science, July, 2000 available on line at http://www.bio.fsu.edu/faculty-easton_actionpotential.htm. The vertical axis of FIG. 18 represents the intensity of a signal applied to a nerve. In FIG. 18, this is represented by voltage but could be represented by charge or current. The horizontal axis represents the length of time during which the signal is applied. The curve represents a threshold curve. Below the curve, the nerve does not excite. Above the curve, the nerve excites. For signals having intensity and duration above the curve, the nerve remains in an excited state and cannot propagate neural impulses (i.e., is effectively blocked).

Using, as an example, a 5,000 Hz signal, such a signal will have a pulse duration (D in FIG. 4) of 100 microseconds assuming there is no time delay between negative and positive pulses. With reference to FIG. 18, such a short pulse duration is associated with a steep-slope portion of the threshold curve requiring a fairly high intensity for an effective signal. In animal studies, applicants have found that signal intensities of 0.5 mA to 8 mA have been effective (recognizing subject-to-subject variability).

Figure 19:
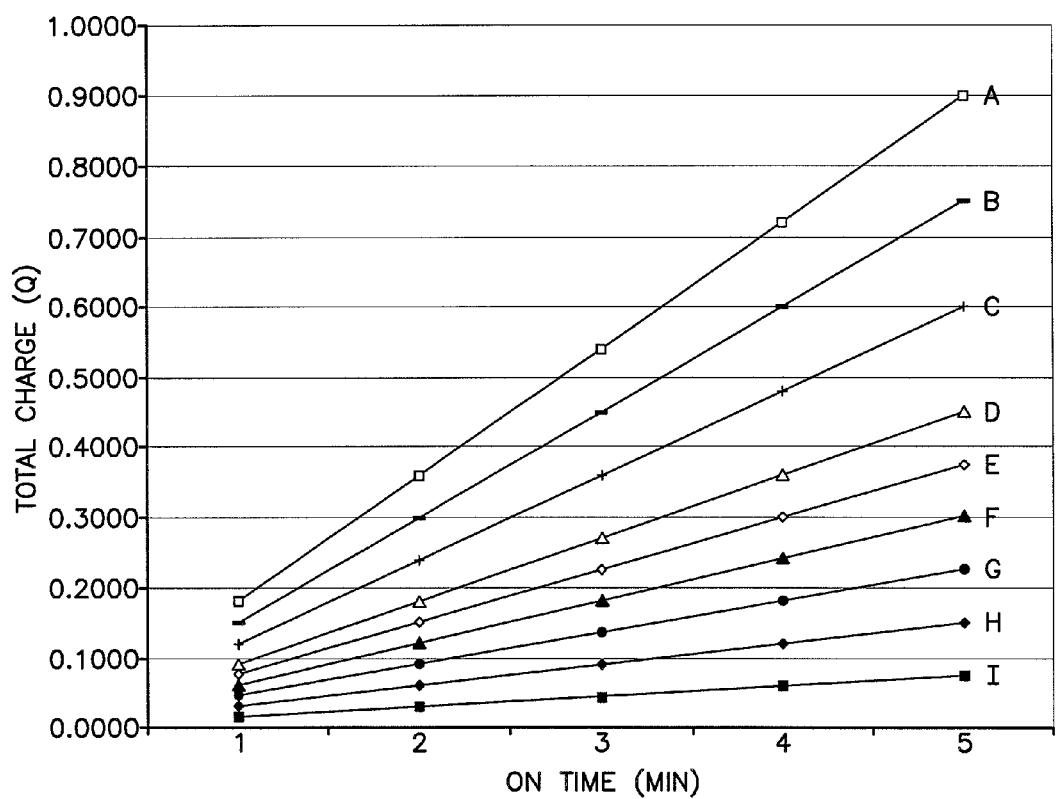
FIG. 19 is a graph illustrating the cumulative amount of charge applied to a nerve under various signal parameters.

Since neural blockage is jointly dependent upon the amount of charge applied to the nerve and the pulse duration of such application, a blocking therapy can be adjusted for a particular patient. FIG. 19 is a graph illustrating the cumulative amount of charge applied to a nerve under various signal parameters. In FIG. 19, the duty cycle (as described above) is a five-minute "on" treatment followed by an "off" period (e.g., five to twenty minutes) during which the nerve may partially recover. The vertical axis is the cumulative amount of charge applied to a nerve during one "on" cycle of five minutes. The horizontal axis is the time point in the "on" cycle. The lines A-I represent the following representative signal parameter options:

A. 6 mA at 5 kHz
B. 5 mA at 5 kHz
C. 4 mA at 5 kHz
D. 6 mA at 2.5 kHz
E. 5 mA at 2.5 kHz
F. 4 mA at 2.5 kHz
G. 3 mA at 2.5 kHz
H. 2 mA at 2.5 kHz
I. 1 mA at 2.5 kHz

With the above, a patient being treated for 2.5 minutes at 6 mA at 5 kHz (line A) and who is tolerating the treatment (no associated discomfort) can have the programmable controller programmed to be treated at 5 mA at 5 kHz (line B). With the line B treatment, the amount charge applied to the nerve over the five minute "on" period is the same as the amount of charge which the patient tolerated for 2.5 minutes of the line A "on" period.

While only 5 kHz and 2.5 kHz options are illustrated in this application, any of the blocking frequencies over 200 Hz could be used. In the examples that follow, the following terms have the following meaning:

1. Electrode configuration No. 1 means the functional circuit of FIG. 1 with the waveforms of either FIG. 4 (with a 5 kHz frequency and a 100 microsecond pulse width and no delay) or FIG. 5 (with a 2.5 kHz frequency and a 100 microsecond pulse width and a delay period DP of 200 microseconds).
2. Electrode configuration No. 2 means the functional circuit of FIG. 3 with the waveforms of either FIG. 6 with either signals on the nerves AVN, PVN being nested (i.e., a delay period on one nerve coincides with pulses on the other nerve) and with the following frequency options:

1. a 5 kHz frequency with the signal of FIG. 6 having a pulse width of 100 microseconds and a delay period of 200 microseconds, or
2. a 2.5 kHz frequency with the signal of FIG. 6 having a pulse width of 100 microseconds and a delay period of 400 microseconds.

Figure 20:
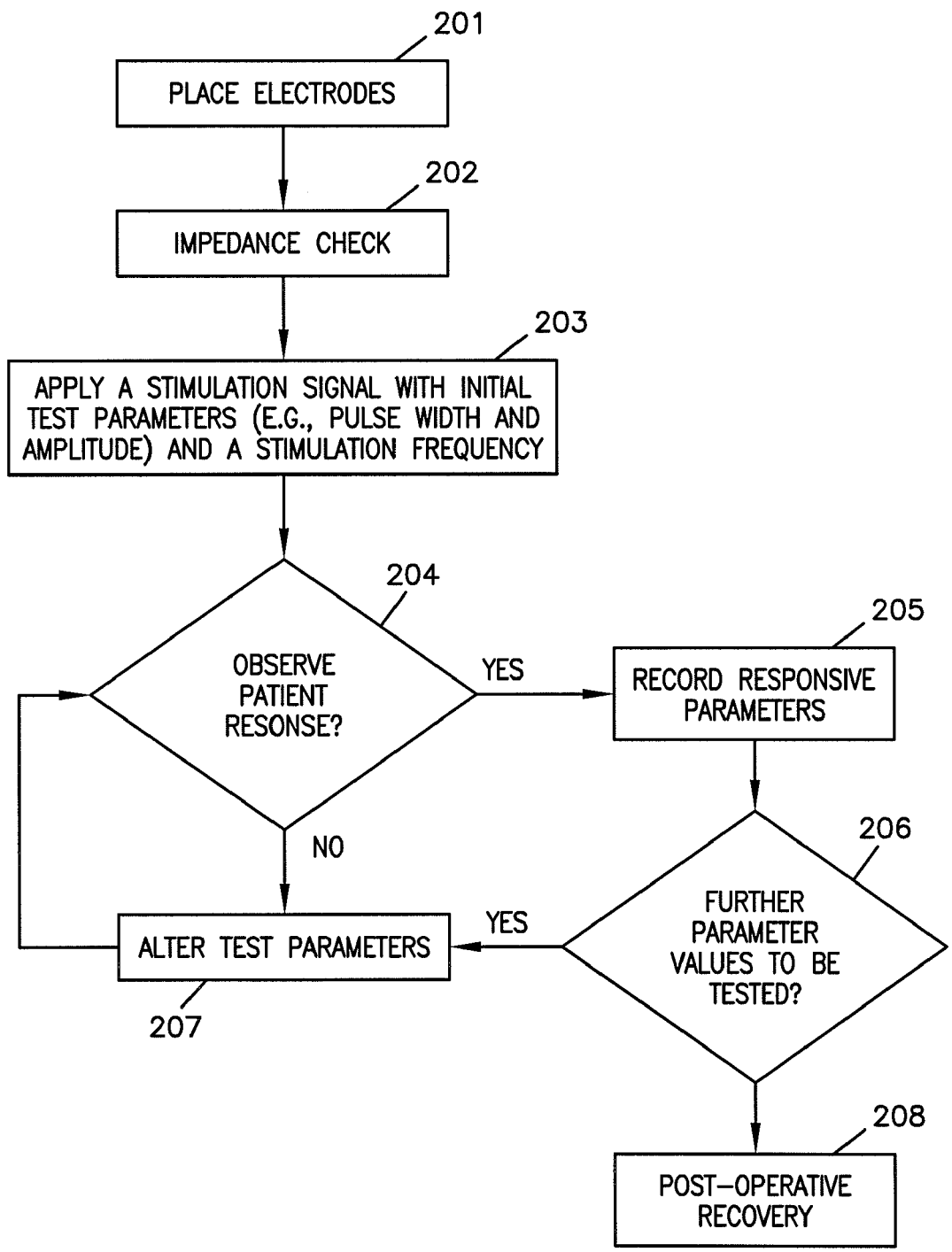
FIG. 20 is a decision tree to determine nerve capture parameters for a particular patient.
Figure 21:
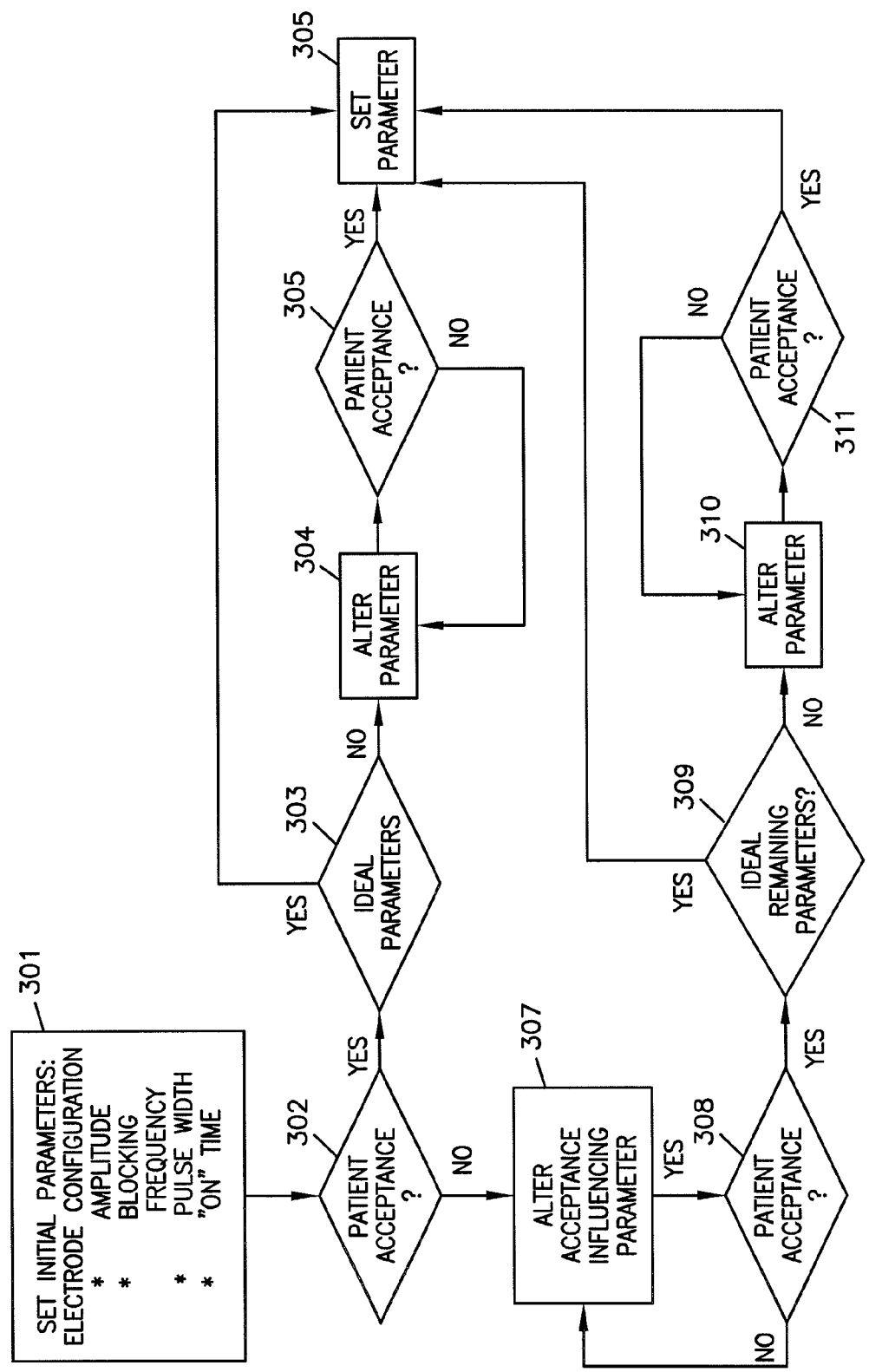
FIG. 21 is a decision tree for setting a programmable controller to therapeutic signal parameters.

FIGS. 20 and 21 illustrate how the foregoing can be used to treat a particular patient. FIG. 20 is a decision tree to assess a patient's responsiveness to certain key parameters.

In FIG. 20, after placement of the electrodes on the nerves AVN, PVN (step 201), the impedance across the electrodes can be measured to assure electrical coupling with the nerves (step 202). If such testing is done during the surgery, the placement may be altered in response to such impedance check.

After such impedance check, an initial stimulation signal can be applied to the electrodes (step 203). Preferably, the programmable controller is set to electrode configuration No. 1 (defined above). Unlike the blocking therapeutic signal, the stimulation signal is set at a low enough frequency to result in a signal applied to the electrodes to be propagated to remote sensing equipment or, more preferably, to an organ of the patient which can be monitored to observe a response to the signal. For example, the stomach can be visually observed to note contractions in response to an applied stimulation signal. Alternatively, the stomach contractions can be measured electronically by sensors on the anodic electrodes placed on the stomach as described above. A representative stimulation signal has a frequency of about 12 Hz.

The stimulation testing of FIG. 20 is to identify values of key parameters (e.g., pulse width and amplitude) for with the particular patient is responsive. These values can then be used in combination with a therapeutic frequency (e.g. over 200 kHz) to treat the patient with a blocking signal. Initially, such parameters can be set at initial target values (e.g., pulse width of 100 microseconds and 2 mA amplitude (as described above for configuration No. 1).

The patient response is observed (step 204). If there is an observed response (e.g., a stomach contraction), the responsive values for the parameters are recorded (step 205). If predetermined ranges of values for such parameters remain to be tested (step 206), the parameters are varied (step 207). For example, amplitude can be increased in value by 1 mA increments while holding pulse duration constant or pulse width can be increased in 100 microsecond increments while holding amplitude constant). After a range of values has been tested (e.g., up to a maximum pulse width of 500 microseconds or a maximum amplitude of 6 mA), the patient is sent to post-operative recovery (step 208.

After any suitable period of post-operative recovery (e.g., fourteen days), the programmable controller can be set to a therapeutic signal parameter as illustrated in the decision tree of FIG. 21. Initial signal parameters are set (step 301). The amplitude and pulse width of the therapeutic signal are preferably selected from those noted as responsive during the testing of FIG. 20. By way of example, the therapeutic signal can be set at a pulse width of 100 microseconds and an amplitude of 4 mA. Blocking frequency and pulse width may be those expected to have greatest likelihood of complete blocking of the nerve (e.g., 5000 Hz and 100 microseconds) and "on" time may be selected to be short-term (e.g., 3 minutes) relative to an anticipated full-term signal application (e.g., 5 minutes).

Patient acceptance of the signal is noted (step 302). Acceptance may be any factor but may include pain or discomfort after a short-term application of the signal. A short-term discomfort is suggestive of discomfort due to signal flow through the esophagus in the configuration of FIG. 1. Also, amplitude may be a discomfort influencing parameter. If patient acceptance is noted in step 302, parameters may be altered to move the parameters to a more ideal setting (step 303 and 304). Ideal may mean a more aggressive treatment (e.g., higher amplitude), a treatment which conserves battery power or otherwise improves operation (e,g,. configuration No. 1, altered "on" time, lower frequency at extended "on" time, etc.). If such altered treatment continues to be acceptable (step 305), the parameters are set as the treatment algorithm. If not, the parameters can be further altered.

If discomfort is noted (step 302), such parameters may be altered in a manner anticipated to improve comfort (step 307). For example, the electrode configuration No. 2 may be selected or amplitude may be reduced. Patient acceptance is noted (step 308) and acceptance influence parameters are further altered until acceptance is noted. Once acceptance is achieved, remaining parameters are compared to ideal and altered (steps 309-311) in a manner as described above with reference to steps 303-305. For example, if the electrode configuration is altered from configuration No. 1 to configuration No. 2 and acceptance is noted, parameters such as amplitude and frequency may be altered as described above.

a. Circuit Schematic

U.S. Pat. No. 6,895,278 (the "'278 patent") to Gordon issued May 17, 2005 teaches systems for measuring signals on neuromuscular tissue in the stomach. The '278 patent is incorporated herein by reference.

Figure 8:
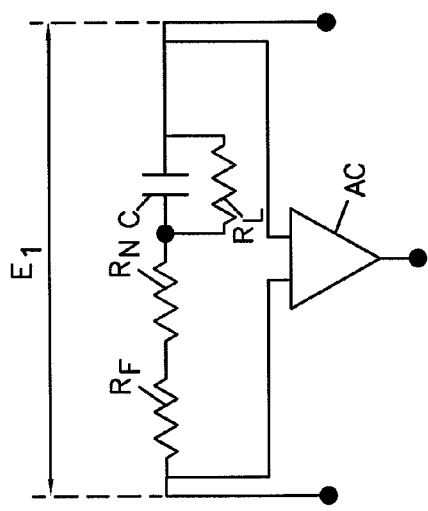
FIG. 8 is an electrical schematic of an electrode on a nerve showing an idealized arrangement for sensing impulses on the nerve.

FIG. 8 is an electrical schematic of the electrode such as electrodes $E_1$ on a nerve with the electrode and nerve shown as circuit components including resistance $R_F$ representing a resistance due to fibrous tissue which grows following application of the electrode to the nerve. It will be appreciated that circuit models such as FIG. 8 are simplifications of a complex physiologic contribution to a circuit.

The resistance $R_F$ may be large after first placement of the electrode on the nerve with the resistance reducing in size or magnitude as fibrous growth occurs. Resistance $R_N$ represents resistance which is a function of the size of the electrode in contact with the nerve. Resistance $R_L$ represents the transmembrane resistance associated with current leakage through the body of the patient. The capacitance C represents a capacitance associated with charge buildup on the surface of the electrode throughout the cycle of the signal application (also known as polarization of the nerve).

Measurement of impedance on the electrode represents conductivity with the nerve since a low impedance suggests an undesired alternative electrical pathway exists in the patient. A very high impedance suggests a broken electrode or other occurrence of non-conductivity.

The circuit of FIG. 8 also includes an amplification circuit AC which will be separately described as an alternative embodiment. Numerous such amplification circuits are known including charge amplification circuits and trans-impedance amplification circuits.

The amplifier AC amplifies a charge across resistance $R_n$ of electrode $E_1$. If a amplifier AC is placed across the resistance of $R_n$, a change in the charge provides an indication of movement of potassium and sodium ions across the cell membranes of the nerve. This provides evidence of depolarization of the nerve.

Accordingly, monitoring of the nerve with a amplifier AC would permit recognizing that the particular set of signal parameters supplied for a particular patient are achieving the desired effect of blocking neural impulses on the nerve. In response to the presence or absence of a detected desired effect, the signal parameters can be modified for a particular patient to achieve the desired effect or to minimize power consumption.

Figure 9:
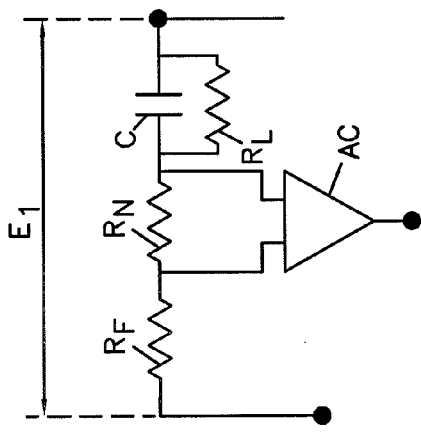
FIG. 9 is the view of FIG. 8 showing a practical arrangement for sensing impulses on the nerve.

As a practical matter, an amplifier AC cannot be placed solely on the $R_n$ but must be placed across the entire electrode as illustrated with reference to the amplifier AC placed on electrode $E_1$ in FIG. 9. Unfortunately, very small changes in charge must be measured to demonstrate the efficacy of the particular signal to depolarize the nerve. The sensitivity of a amplifier AC increases as the capacitance C is decreased. Accordingly, increasing the surface area of the electrode (thereby increasing the capacitance C, decreasing impedance and reducing noise contribution of the electrode) increases a likelihood of reliable data being attained with a charge amplifier CA.

b. Capacitance

Figure 10:
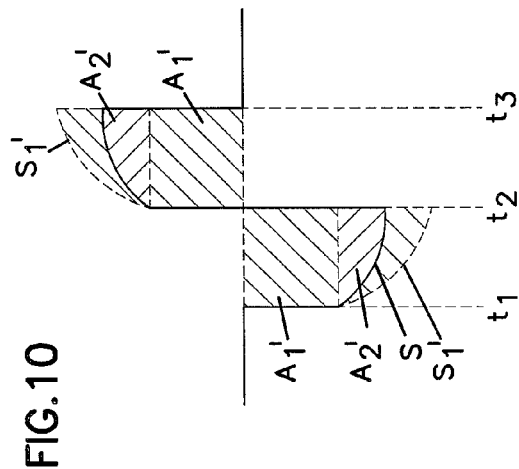
FIG. 10 is a graphical representation of a pulse cycle waveform modified to illustrate an effect of a capacitance associated with a charge buildup on the surface of an electrode.

While the waveforms in FIGS. 4, 5 and 6 and 7 are shown as square waveforms, it will be appreciated that a true square shape is not achieved in a natural embodiment such as application of electrodes to a nerve. FIG. 10 illustrates a truer representation of the shape of the waveform resulting from the capacitance C associated with charge buildup on the surface of the electrode using a constant current output.

As shown in FIG. 10, the signal is initiated at time $T_1$. Between times $T_1$ and $T_2$, there is a sloped surface S associated with buildup of charge on the surface of the electrode. After the charge has achieved a maximum charge to permit discharge of the capacitance on the electrode (e.g., at $T_2$) the pulse reverses and a complimentary shaped slope S occurs on the second pulse.

The waveform includes a square area component $A_1'$ and a component $A_2'$ between the square component $A_1'$ and bounded by the slope S. The square component $A_1'$ represents the amount of energy that is being applied to the nerve by the electrode. The remainder of the area $A_2'$ represents wasted energy which is consumed during the pulse but which is absorbed at the electrode-tissue interface and, therefore, not contributing energy to the nerve system.

The volume of the wasted energy component $A_2'$ varies with the capacitance of the electrode. A small capacitance is associated with a large electrode surface area illustrated by the solid curve S. A small electrode surface area is associated with a larger capacitance illustrated by the surface area $S_1$. Therefore, as illustrated in FIG. 10, a large electrode surface area results in the smallest amount of wasted energy.

It is desirable to minimize the amount of wasted energy. Such waste unnecessarily consumes battery power. Accordingly, the amount of wasted energy can minimize by maximizing the surface area of the electrode.

Figure 11:
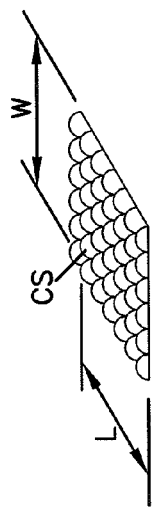
FIG. 11 is a perspective view of an electrode surface.

FIG. 11 illustrates an electrode E having a contact surface area CS which is the product of the length L and the width W of the electrode. It will be appreciated that while the electrode E is shown in FIG. 11 as having a flat contact surface CS the electrode E can be curved to increase the amount of contact area between the electrode E and the nerve on which the electrode is placed. The contact surface CS of the electrode E in FIGS. 11, 12 is shown as a flat smooth surface which will have a characteristic capacitance.

Figure 12:
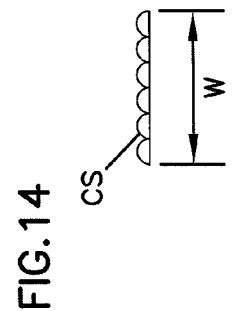
FIG. 12 is an end elevation view of the electrode of FIG. 11.
Figure 13:
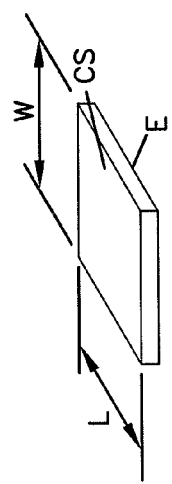
FIG. 13 is a perspective view of an electrode surface modified with nano-particles on the surface.
Figure 14:
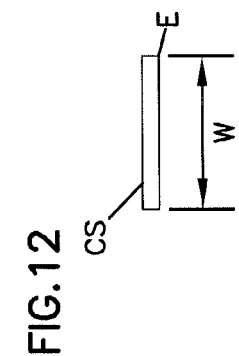
FIG. 14 is an end elevation view of the electrode of FIG. 13.

FIGS. 13 and 14 illustrate a modification to the contact surface where the electrode E' of FIGS. 13 and 14 has identical length and width of the electrode E of FIGS. 11 and 12 but has a surface treatment to greatly increase the contact surface CS' of the electrode E'.

The surface CS' is formed by nano technology placement of nano-particles. Since the nano-particles appear on the surface CS' as beads having arcuate individual surfaces, the combined surface area is greatly increased over the flat smooth surface area of FIG. 11.

Figure 15:
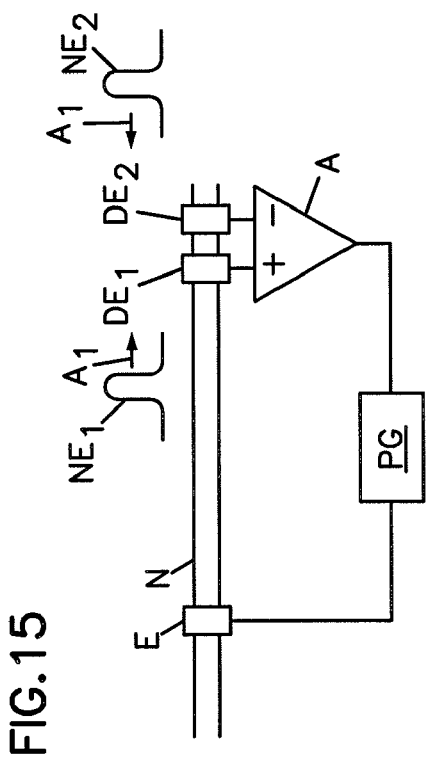
FIG. 15 is a circuit schematic view of an electrode on a nerve with a nerve pulse detection circuit.

The surface area CS could be increased by any technique which roughens the surface CS. However, the spaces between the modules may be filled with fibrosis which presents a resistance between opposing surfaces. Through use of nano-application of nano-beads, very small separation occurs. The small separation is so small the surface appears smooth and presents an atraumatic surface to opposing tissue. The use of nano-technology to increase a surface area of an electrode to alter its capacitance is known for cochlear implants c. Controlling Therapy in Response to Detected Neural Activity FIG. 15 illustrates detecting neural impulses along the nerve and modifying an application to an electrode based on the detected impulses. In FIG. 15, the nerve is illustrated as N. A therapy application electrode is illustrated as E and a signal source (such as a pulse generator with logic and control circuits) is indicated as PG.

A first detection electrode $DE_1$ is positioned on the nerve as is a second detection electrode $DE_2$. The first detection electrode $DE_1$ is positioned between the therapy electrode E and the second detection electrode $DE_2$. The detection electrodes $DE_1$ and $DE_2$ are connected to an amplifier placed in close proximity to the electrodes $DE_1$ and $DE_2$. The amplifier has an output connected to the logic of the pulse generator PG.

Neural impulses are illustrated in FIG. 15 as a first neural impulse $NE_1$ which is propagating in a direction from the therapy electrode E to the first detection electrode $DE_1$. The direction of travel of the first propagation signal $NS_1$ is labeled $A_1$. The second neural signal $NS_2$ travels along the nerve in the opposite direction illustrated by arrow $A_2$.

In the event it is desirable to block neural impulses traveling along the direction of arrow $A_2$, as neural impulses pass electrode $DE_2$, they pass a signal to the amplifier A. After a very short period of time (representing the time for a neural impulse to travel the distance between electrodes $DE_2$ and $DE_1$), the pulse $NE_2$ passes electrode $DE_1$ generating a further impulse which is amplified by the amplifier A. The output from the amplifier A is again sent to the pulse generator which can compare the signals indicating that a neural impulse $NE_2$ is traveling in the direction of arrow $A_2$. Recognizing such neural activity in the undesired direction, the pulse generator can then energize the electrode E with a blocking signal selected to block the nerve N and block the neural impulses from passing the electrode E.

The apparatus of FIG. 15 can also be used to control a blocking signal. Namely, the specific parameters of the blocking signal to the electrode E can be modified by the pulse generator PG in response to detection of neural impulses $NS_1$ traveling in the direction of arrow $A_1$. The presence of such neural impulses indicates that the blocking signal for the particular patient is not optimized and the blocking parameters can be adjusted as desired to optimize the blocking effect at therapeutic electrode E.

Since neural impulses pass along a nerve at known speeds, preferably, the amplifier A is positioned in very close proximity to the electrodes $DE_1$ and $DE_2$ so that the amplifier A can detect the signals and provide an amplified signal to the pulse generator in time to present an appropriate blocking signal (or stimulation signal) to the therapeutic electrode E.

Figure 16:
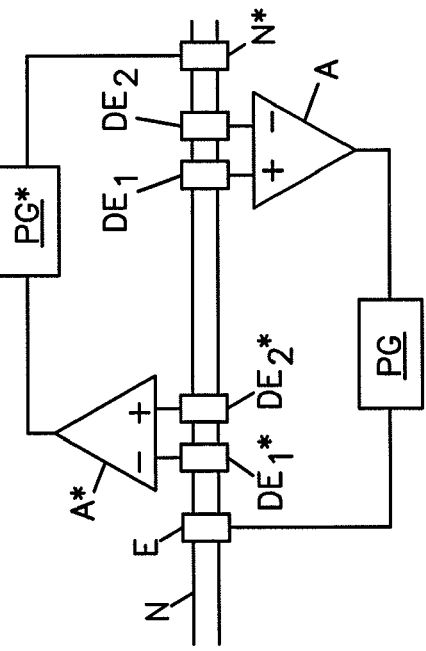
FIG. 16 is the view of FIG. 15 showing two detection circuits on the nerve.

FIG. 16 illustrates two circuits of FIG. 15 placed on a nerve. The elements of the second circuit are identical to the first with the addition of an asterisk to distinguish the circuits.

Figure 17:
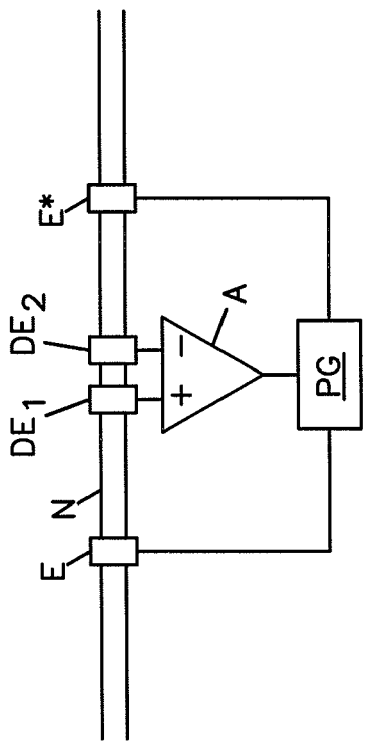
FIG. 17 is a circuit schematic view of the functional equivalent of FIG. 16 but with simplified circuitry.

Two circuits on a nerve permit detection and control on both afferent and efferent nerve fibers. FIG. 17 is the functional equivalent of FIG. 16 but with simplified circuitry. Unlike previously described embodiments which block the nerve at all times during application of the blocking signal (and during a neural recovery period), the embodiments of FIGS. 15-17 are impulse targeted blocking.

The polarity of the amplified signal provides a determination of the nerve signal. By applying a polarity discriminator, the direction of the signal can be determined with a single amplifier system and appropriate action of programmable direction blocking can be taken.

With the foregoing detailed description of the present invention, it has been shown how the objects of the invention have been attained in a preferred manner. Modifications and equivalents of disclosed concepts such as those which might readily occur to one skilled in the art, are intended to be included in the scope of the claims which are appended hereto.

What is claimed is:

1. An apparatus for applying a signal to a nerve for the treatment of a disorder, said apparatus comprising:
   a first electrode and a second electrode, each adapted to be secured to a vagus nerve of a patient;
   a first anode connected to the first electrode and a second anode connected to the second electrode;
   a signal generator electrically connected to each of said first and second electrodes;
      said signal generator providing for selection of a first and a second waveform, a pulse duration, and a duty cycle comprising an on period and an off period; and
      said signal generator adapted to create the first waveform at the first electrode and the second waveform at said second electrode, wherein each of said first and second waveforms have parameters selected to block propagation of neural action potentials; wherein the parameters comprise a duty cycle, wherein said on period comprises a repeating pattern of cycles of pulses and a delay period between at least selected ones of said cycles of pulses, wherein each cycle of pulses includes at least a negative pulse and a positive pulse, and wherein said delay period is less than a time period identified as sufficient for a recovery of the vagus nerve from a neural block induced by said cycle; and wherein said first and second waveforms are out of phase with each other such that during each on period a cycle of one of said waveforms occurs during the delay period of the other of said waveforms.

2. The apparatus according to claim 1, wherein said delay period is at least equal to a time interval of one complete cycle.

3. The apparatus of according to claim 1, wherein the delay period of the first waveform is equal to the cycle time of the second waveform.

4. The apparatus according to claim 1, wherein said waveforms have an amplitude between 0.5 mA and 8 mA.

5. The apparatus according to claim 1, wherein said waveforms have a cycle frequency in excess of 250 Hz.

6. The apparatus according to claim 5, wherein said waveforms have a cycle frequency of at least 2500 Hz.

7. The apparatus according to claim 1, wherein the on time is at least 2 minutes.

8. The apparatus according to claim 7, wherein the off time is at least 5 minutes.

9. The apparatus according to claim 1, wherein the total cumulative charge delivered to the nerve during an on time is at least 0.1000 coulombs.

10. The apparatus according to claim 1 wherein said electrodes include a contact surface area enhanced by a surface treatment selected to increase said surface area by creating a plurality of protuberances with opposing surfaces of protuberances sized to present an atraumatic surface to opposing tissue.

11. The apparatus according to claim 10, wherein the surface of the electrodes is enhanced with nanoparticles.

12. The apparatus according to claim 1, wherein the first and second anodes are placed on the same vagus nerves as the first and second electrodes respectively.

13. The apparatus according to claim 1, wherein the first and second anodes are placed on the stomach.

14. The apparatus according to claim 1, wherein the first and second electrodes are each placed on the esophagus.

15. The apparatus according to claim 1, wherein the first electrode is placed on the anterior vagus nerve and the second electrode is placed on the posterior vagus nerve.

16. The apparatus according to claim 1, further comprising a signal amplifier connected across at least one of said electrodes and selected to identify a depolarization of a nerve.

17. A method for the treatment of a disorder susceptible to down-regulation of neural activity, said method comprising:
   placing a first electrode on said first vagal nerve and a second electrode on said vagal second nerve;
   connecting a first anode to the first electrode and placing the first anode on or near said first vagus nerve at a location that differs from the location of the first electrode, and connecting a second anode to the second electrode and placing the second anode on or near the second electrode at a location that differs from the second electrode;
   electrically connecting a signal generator to each of said first and second electrodes; said signal generator adapted to create a signal having a first waveform at said first electrode and a second waveform at said second electrode, wherein each of said first and second waveforms have parameters selected to block propagation of neural action potentials; wherein the parameters comprise an "on" period and an "off" period, wherein said "on" period comprises a repeating pattern of cycles of pulses and a delay period between at least selected ones of said cycles of pulses, wherein each cycle of pulses includes at least a negative pulse and a positive pulse and wherein said delay period is less than a time period identified as sufficient for a recovery of the vagus nerve from a neural block induced by said cycle; and wherein said first and second waveforms are out of phase with each other such that during each "on" period a cycle of one of said waveforms occurs during a delay period of the other of said waveforms; and
   activating said signal generator to apply said waveforms to said first and second nerves.

18. The method according to claim 17, wherein said delay period is at least equal to a time interval of one complete cycle.

19. The method of according to claim 17, wherein the delay period of the first waveform is equal to the cycle time of the second waveform.

20. The method according to claim 17, wherein said waveforms have an amplitude between 0.5 mA and 8 mA.

21. The method according to claim 17, wherein said waveforms have a cycle frequency in excess of 250 Hz.

22. The method according to claim 17, wherein the on time is at least 2 minutes.

23. The method according to claim 17, wherein the off time is at least 5 minutes.

24. The method according to claim 17, wherein the first and second anodes are placed on the same vagus nerves as the first and second electrodes respectively.

25. The method according to claim 17, wherein the first and second anodes are each placed on the stomach.

26. The method according to claim 17, wherein the first and second electrodes are each placed on the esophagus.

27. The method according to claim 17, wherein the first electrode is placed on the anterior vagus nerve and the second electrode is placed on the posterior vagus nerve.

\* \* \* \* \*